(12) United States Patent
Tuksar et al.

(10) Patent No.: US 9,630,952 B2
(45) Date of Patent: Apr. 25, 2017

(54) CRYSTALLINE FORMS OF AFATINIB DI-MALEATE

(71) Applicant: IVAX INTERNATIONAL GMBH, Rapperswil (CH)

(72) Inventors: Mihaela Tuksar, Cakovec (HR); Marina Ratkaj, Zagreb (HR); Miroslav Zegarac, Zagreb (HR)

(73) Assignee: Ivax International GmbH, Rapperswil (CH)

(*) Notice: Subject to any disclaimer, the term of this patent is extended or adjusted under 35 U.S.C. 154(b) by 0 days.

(21) Appl. No.: 14/990,345

(22) Filed: Jan. 7, 2016

(65) Prior Publication Data

US 2016/0122329 A1    May 5, 2016

Related U.S. Application Data

(63) Continuation of application No. PCT/US2015/010013, filed on Jan. 2, 2015.

(60) Provisional application No. 61/922,982, filed on Jan. 2, 2014, provisional application No. 61/932,317, filed on Jan. 28, 2014, provisional application No. 62/016,155, filed on Jun. 24, 2014.

(51) Int. Cl.
   *A61K 31/517*   (2006.01)
   *C07D 405/12*   (2006.01)
   *C07C 55/08*    (2006.01)

(52) U.S. Cl.
   CPC ............ *C07D 405/12* (2013.01); *C07C 55/08* (2013.01)

(58) Field of Classification Search
   USPC ...................... 544/293; 514/266.24
   See application file for complete search history.

(56) References Cited

U.S. PATENT DOCUMENTS

| RE43,431 E | 5/2012 | Himmelsbach et al. |
| 8,426,586 B2 | 4/2013 | Soyka et al. |
| 2005/0085495 A1* | 4/2005 | Soyka .................. C07D 405/12 514/266.24 |

FOREIGN PATENT DOCUMENTS

| WO | WO 02/50043 A1 | 6/2002 |
| WO | WO 2005/037824 A2 | 4/2005 |
| WO | WO2012/121764 * | 9/2012 |
| WO | WO 2012/121764 A1 | 9/2012 |
| WO | WO 2013/052157 A1 | 4/2013 |

OTHER PUBLICATIONS

Brittain's publication, crystalline and pharmaceutical composition, 1999, pp. 348-361.*
Caira; "Crystalline Polymorphism of Organic Compounds"; Topics in Current Chemistry; vol. 198; 1998; p. 163-208.
Jordan; "Tamoxifen: A Most Unlikely Pioneering Medicine"; Nature Reviews, Drug Discovery; vol. 2; Mar. 2003; p. 205-213.
Hackam et al.; "Translation of Research Evidence From Animals to Humans"; JAMA; vol. 296 No. 14; Oct. 2006; p. 1731-1732.

* cited by examiner

*Primary Examiner* — Rei-Tsang Shiao
(74) *Attorney, Agent, or Firm* — Baker & Hostetler LLP

(57) ABSTRACT

The present disclosure encompasses crystalline forms of Afatininb di-maleate and methods of their use.

4 Claims, 18 Drawing Sheets

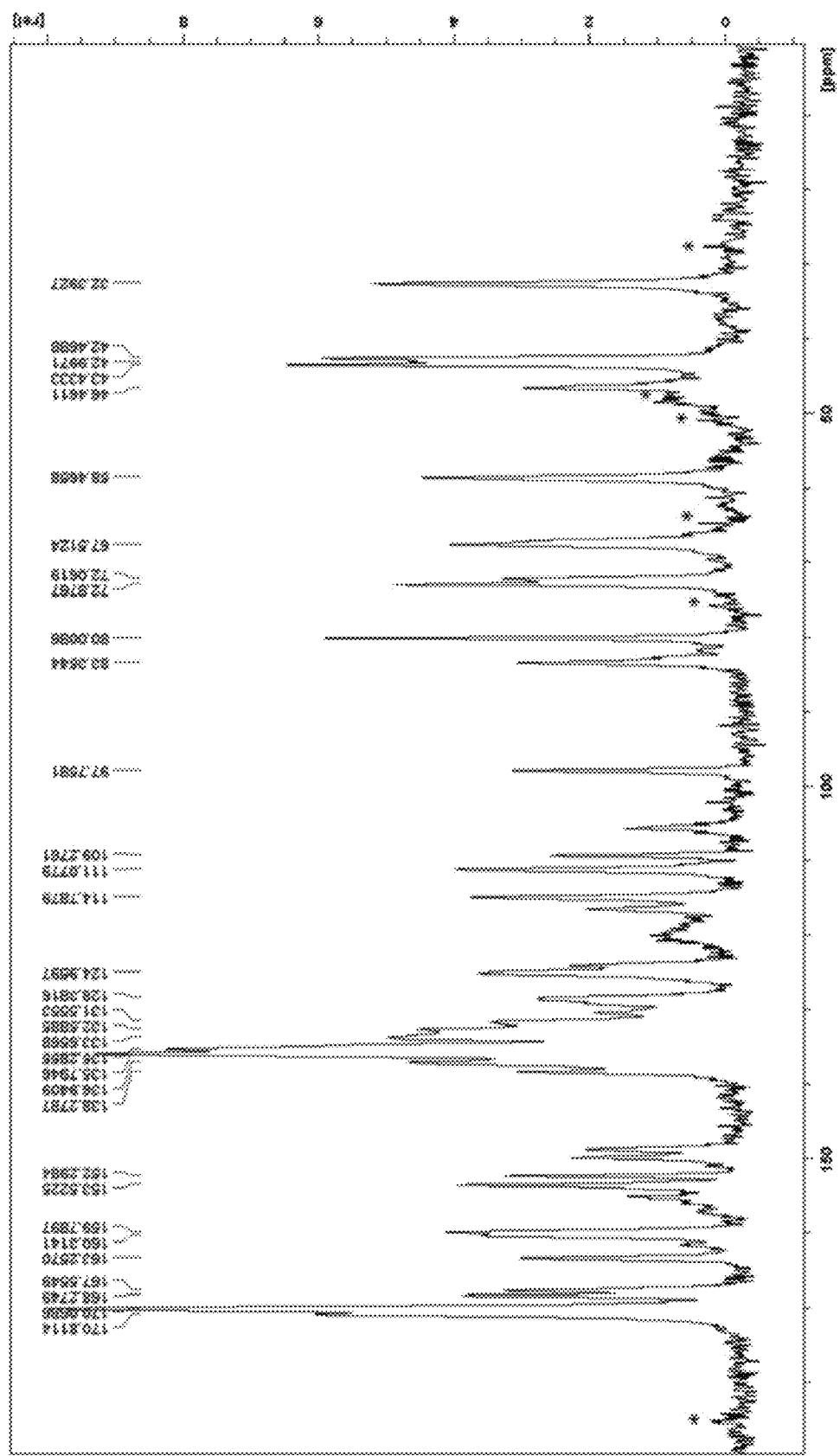
Figure 13. ssNMR spectrum of Afatinib dimaleate Form M.

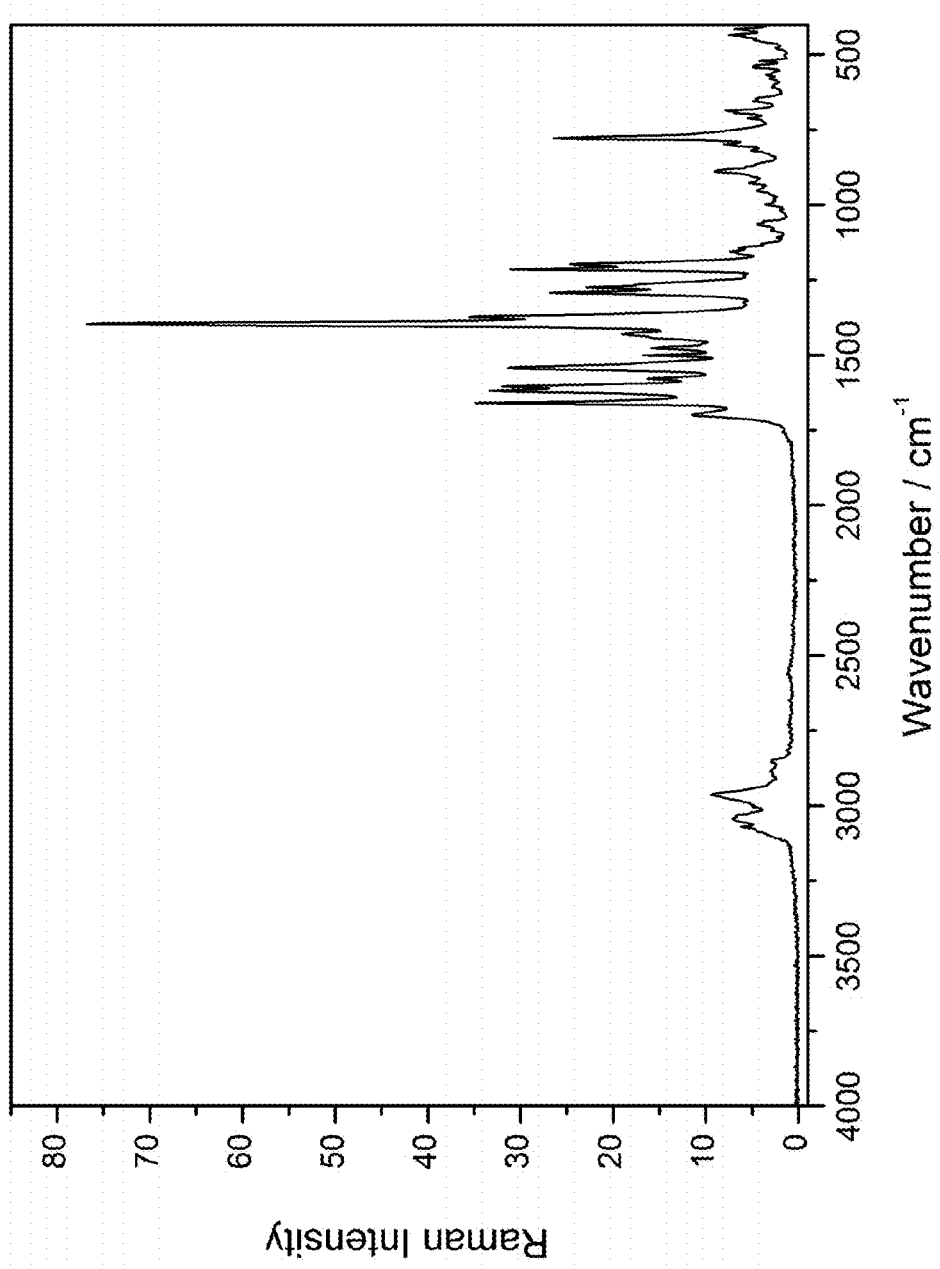
Figure 14. Raman spectrum of Afatinib dimaleate Form M.

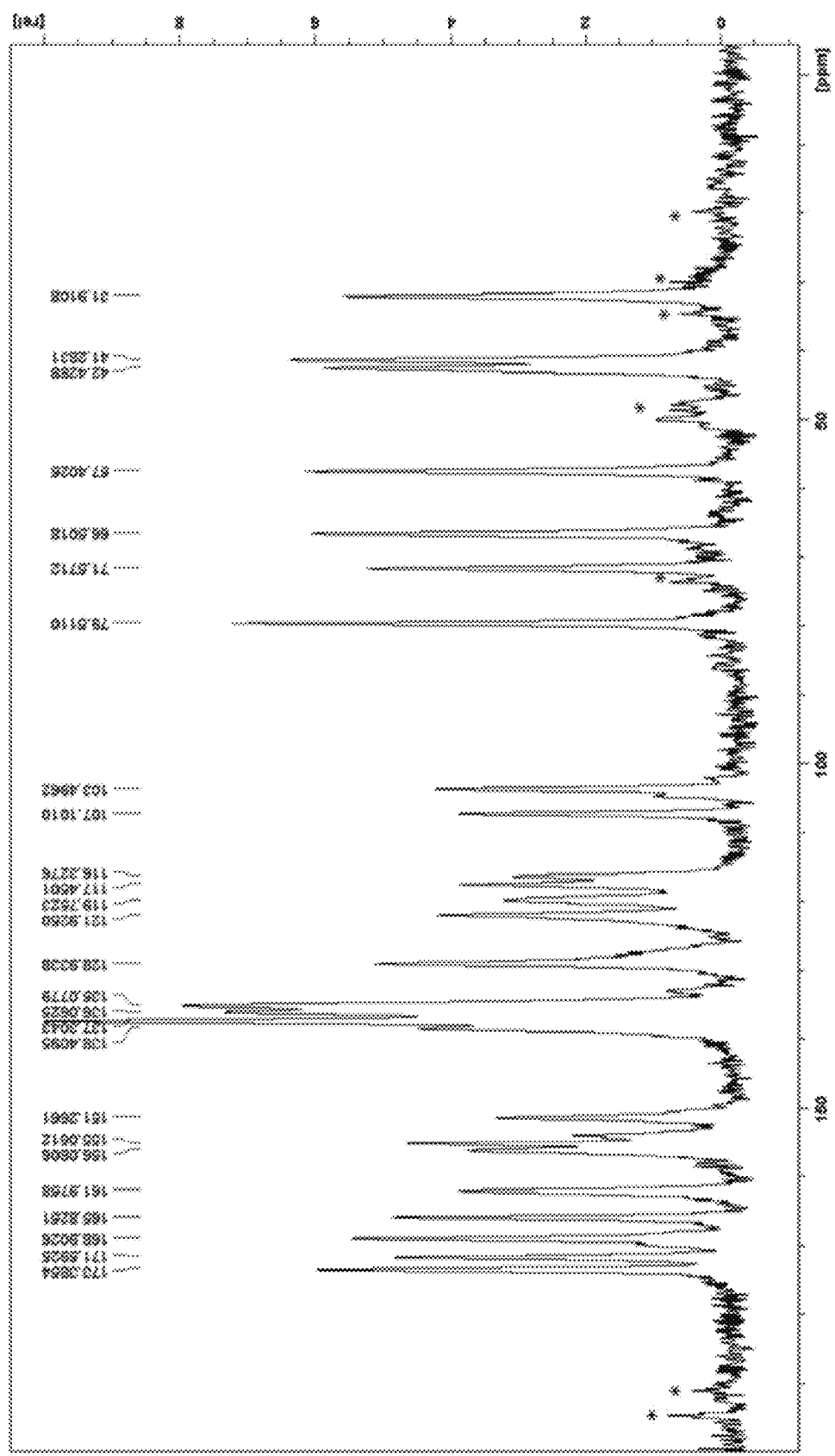
Figure 15. ssNMR spectrum of Afatinib dimaleate Form N.

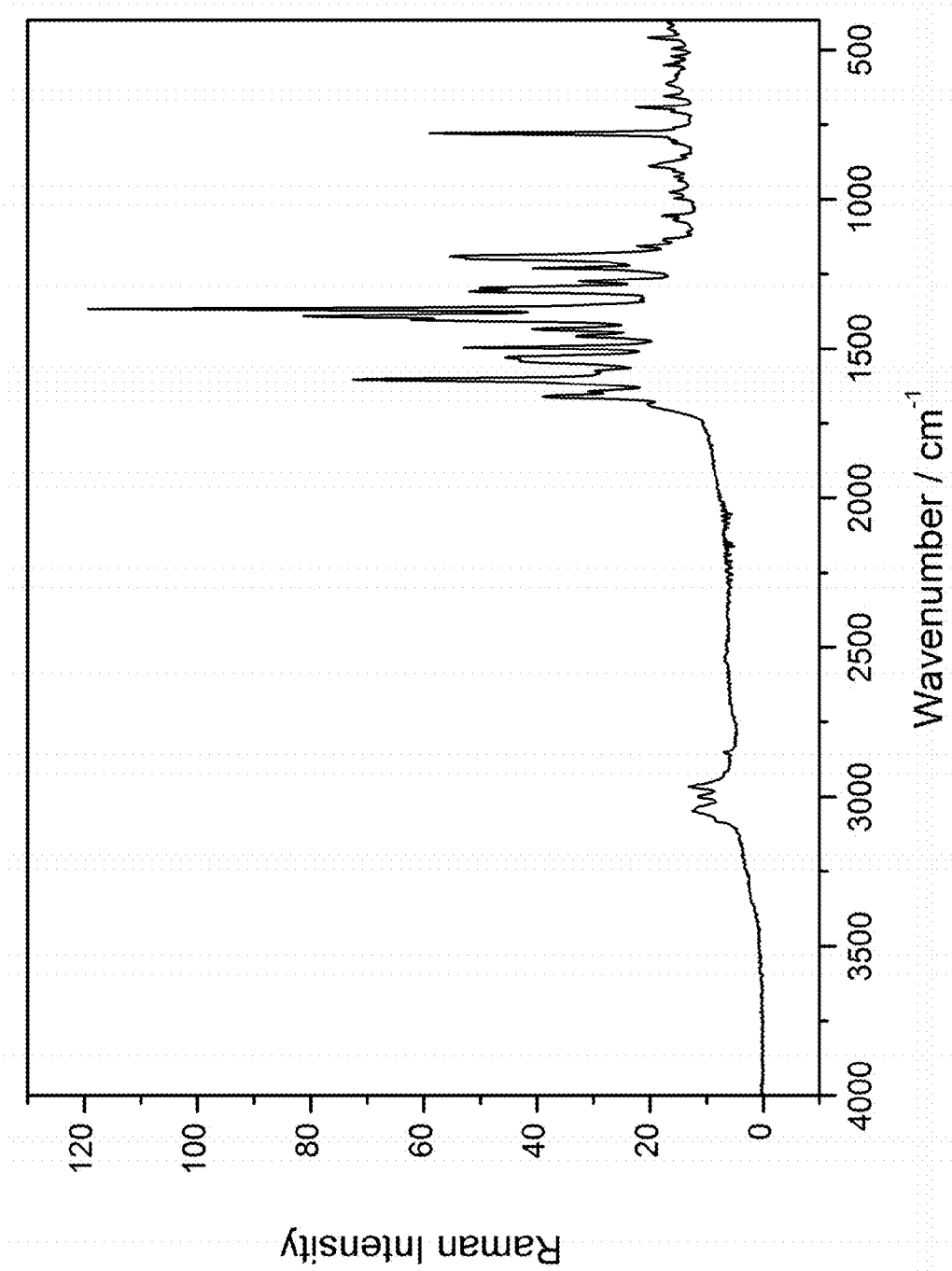
Figure 16. Raman spectrum of Afatinib dimaleate Form N.

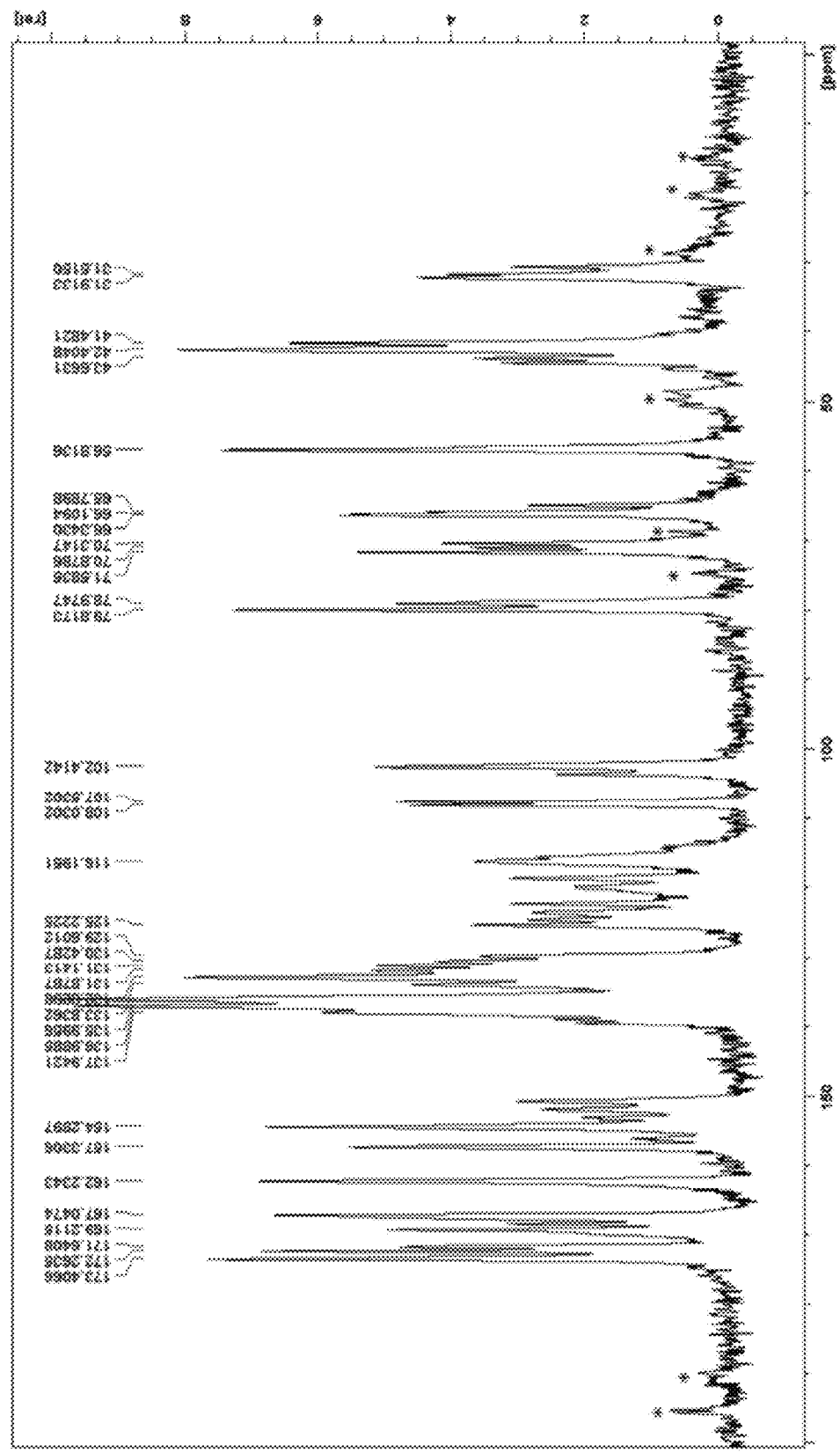
Figure 17. ssNMR spectrum of Afatinib dimaleate Form Alpha.

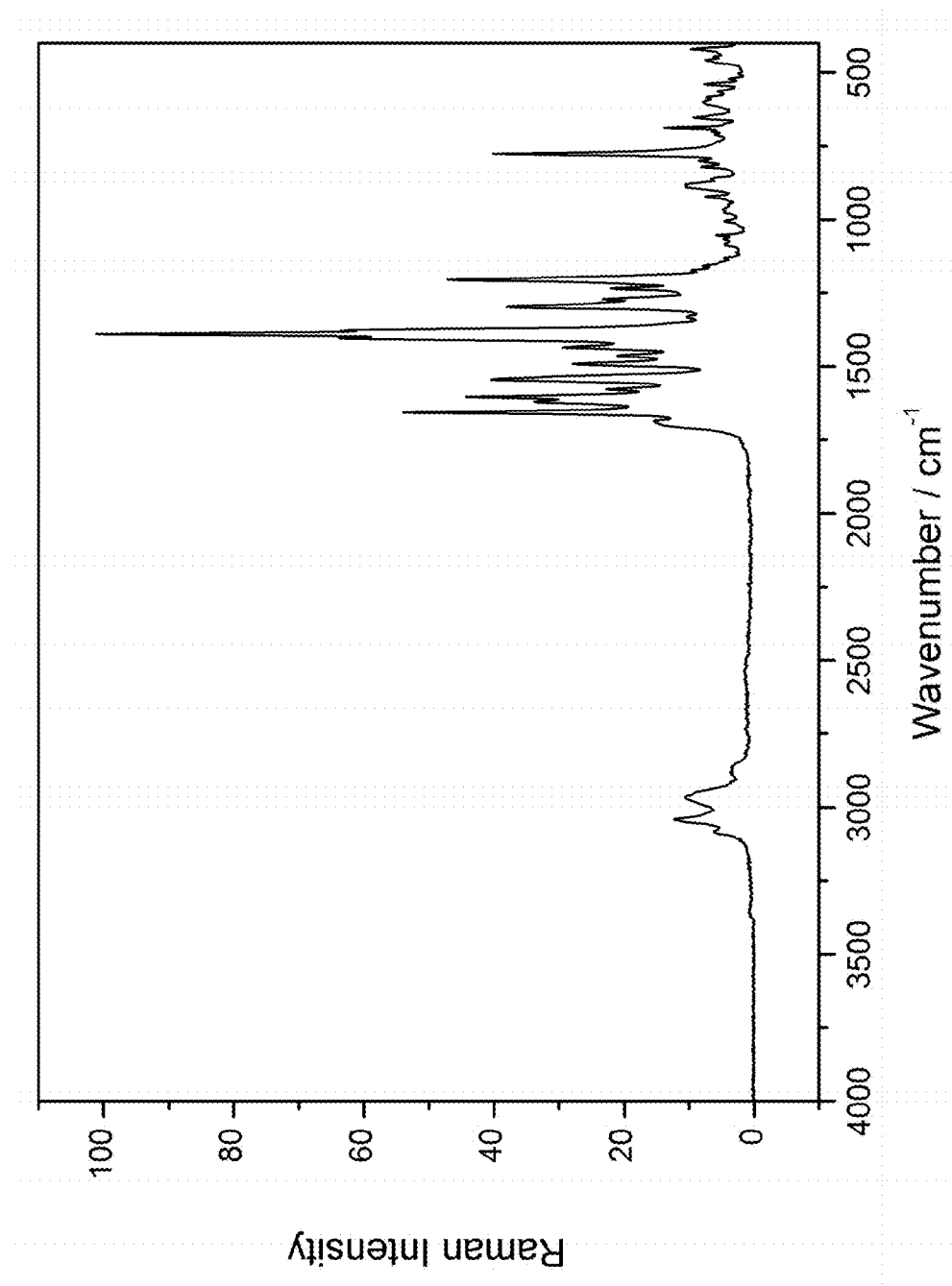
Figure 18. Raman spectrum of Afatinib dimaleate Form Alpha.

CRYSTALLINE FORMS OF AFATINIB DI-MALEATE

CROSS REFERENCE TO RELATED APPLICATIONS

This application is a continuation of International Application No. PCT/US2015/010013, filed Jan. 2, 2015, which claims the benefit of U.S. Provisional Application Nos. 61/922,982, filed Jan. 2, 2014; 61/932,317, filed Jan. 28, 2014; and 62/016,155, filed Jun. 24, 2014, the entireties of which are incorporated by reference herein.

FIELD OF THE DISCLOSURE

The present disclosure encompasses crystalline forms of Afatininb di-maleate.

BACKGROUND OF THE DISCLOSURE

The compound N-[4-[(3-Chloro-4-fluorophenyl)amino]-7-[[(3S)-tetrahydro-3-furanyl]oxy]-6-quinazolinyl]-4(dimethylamino)-2-butenamide, known as Afatinib, has the following structural formula:

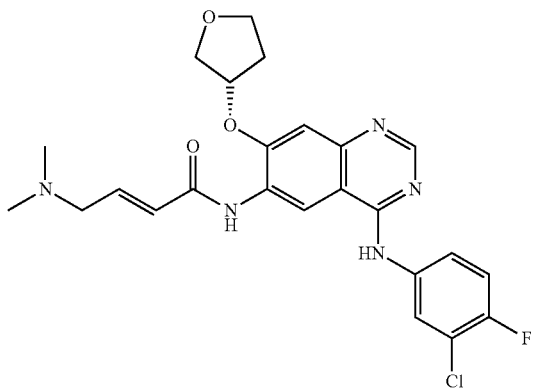

Afatinib is formulated in the form of its dimaleate salt and marketed under the name GILOTRIF™ (US). GILOTRIF is a kinase inhibitor indicated for the first-line treatment of patients with metastatic non-small cell lung cancer (NSCLC) whose tumors have epidermal growth factor receptor (EGFR) exon 19 deletions or exon 21 (L858R) substitution mutations as detected by an FDA-approved test.

Afatinib, its salt and solid state forms thereof are described in USRE 43, 431, U.S. Pat. No. 8,426,586, WO2012/121764 and WO2013/052157.

Polymorphism, the occurrence of different crystalline forms, is a property of some molecules and molecular complexes. A single molecule may give rise to a variety of polymorphs having distinct crystal structures and physical properties like melting point, thermal behaviors (e.g. measured by thermogravimetric analysis—"TGA", or differential scanning calorimetry—"DSC"), X-ray diffraction pattern, infrared absorption fingerprint, and solid state ($^{13}C$-) NMR spectrum. One or more of these techniques/parameters may be used to distinguish different polymorphic forms of a compound.

Different salts and solid state forms (including solvated forms) of an active pharmaceutical ingredient may possess different properties. Such variations in the properties of different salts and solid state forms and solvates may provide a basis for improving formulation, for example, by facilitating better processing or handling characteristics, changing the dissolution profile in a favorable direction, or improving stability (polymorph as well as chemical stability) and shelf-life. These variations in the properties of different salts and solid state forms may also offer improvements to the final dosage form, for instance, if they serve to improve bioavailability. Different salts and solid state forms and solvates of an active pharmaceutical ingredient may also give rise to a variety of polymorphs or crystalline forms, which may in turn provide additional opportunities for fine-tuning the properties and characteristics of a solid active pharmaceutical ingredient.

Discovering new solid state forms and solvates of a pharmaceutical product may yield materials having desirable processing properties, such as ease of handling, ease of processing, storage stability, and ease of purification or as desirable intermediate crystal forms that facilitate conversion to other polymorphic forms. New solid state forms of a pharmaceutically useful compound can also provide an opportunity to improve the performance characteristics of a pharmaceutical product. It enlarges the repertoire of materials that a formulation scientist has available for formulation optimization, for example by providing a product with different properties, e.g., a different crystal habit, higher crystallinity or polymorphic stability which may offer better processing or handling characteristics, improved dissolution profile, or improved shelf-life (chemical/physical stability). For at least these reasons, there is a need for additional solid state forms (including solvated forms) of Afatinib di-maleate.

SUMMARY OF THE DISCLOSURE

The present disclosure provides solid state forms of Afatinib di-maleate, and pharmaceutical compositions thereof.

The present disclosure also encompasses the use of Afatinib di-maleate forms of the present disclosure for the preparation of other Afatinib salts, or of Afatinib base, solid state forms and/or pharmaceutical compositions thereof.

The present disclosure also encompasses the solid state forms of Afatinib di-maleate for use in the preparation of pharmaceutical compositions.

The present disclosure also encompasses the use of Afatinib di-maleate solid state forms of the present disclosure for the preparation of pharmaceutical compositions.

The present disclosure comprises a process for preparing the above mentioned pharmaceutical compositions. The process comprises combining the Afatinib di-maleate solid state forms according to the disclosure with at least one pharmaceutically acceptable excipient.

The solid state forms and the pharmaceutical compositions of Afatinib di-maleate of the present disclosure can be used as medicaments, particularly for the treatment of non-small cell lung cancer (NSCLC).

The present disclosure also provides a method for treating non-small cell lung cancer (NSCLC), comprising administering a therapeutically effective amount of Afatinib di-maleate solid state forms according to the disclosure, or at least one of the above pharmaceutical compositions according to the disclosure, to a subject suffering from non-small cell lung cancer (NSCLC).

BRIEF DESCRIPTION OF THE DRAWINGS

FIG. 13 shows a $^{13}$C NMR spectrum of Afatinib dimaleate Form M.

FIG. 14 shows a Raman spectrum of Afatinib dimaleate Form M.

FIG. 15 shows a $^{13}$C NMR spectrum of Afatinib dimaleate Form N.

FIG. 16 shows a Raman spectrum of Afatinib dimaleate Form N.

FIG. 17 shows a $^{13}$C NMR spectrum of Afatinib dimaleate Form Alpha.

FIG. 18 shows a Raman spectrum of Afatinib dimaleate Form Alpha.

DETAILED DESCRIPTION OF THE DISCLOSURE

Figure 1:
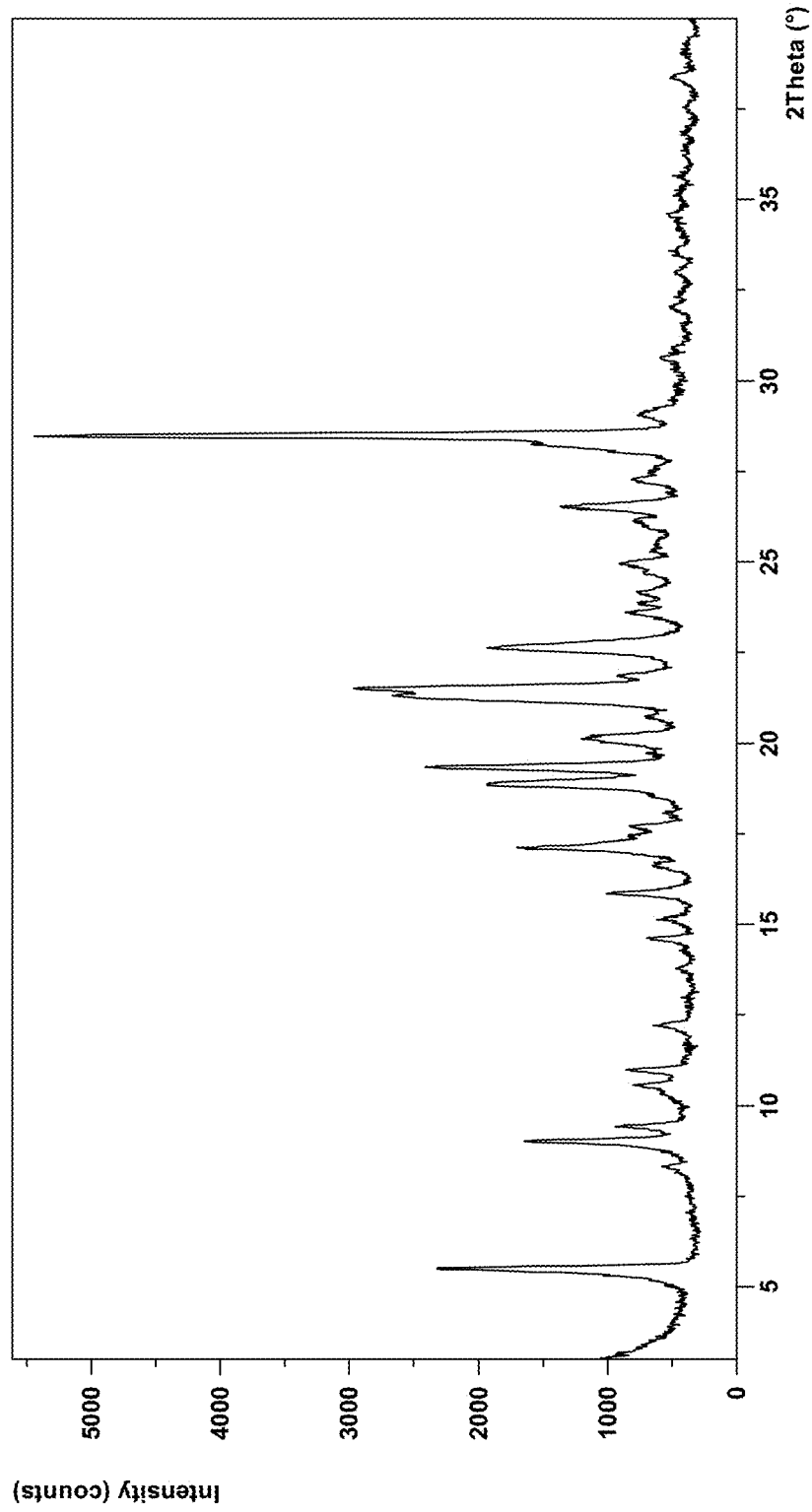
FIG. 1 shows an X-ray powder diffractogram of Afatinib di-maleate Form G.

The present disclosure encompasses solid state forms of Afatinib di-maleate. Solid state properties of Afatinib di-maleate can be influenced by controlling the conditions under which the Afatinib di-maleate is obtained in solid form.

In some embodiments, the crystalline form of Afatinib di-maleate of the disclosure is substantially free of any other forms of Afatinib di-maleate, or of specified polymorphic forms of Afatinib di-maleate, respectively.

As used herein, the term "substantially free" means that the solid state forms of the present disclosure contain 20% (w/w) or less of other polymorphic forms, or of a specified polymorph of Afatinib di-maleate. According to some embodiments, the salts and solid state forms of the present disclosure contain 10% (w/w) or less, 5% (w/w) or less, 2% (w/w) or less, 1% (w/w) or less, 0.5% (w/w) or less, or 0.2% (w/w) or less of other polymorphs, or of any specified polymorphic forms of Afatinib di-maleate. In other embodiments, the solid state forms of Afatinib di-maleate of the present disclosure contain from 1% to 20% (w/w), from 5% to 20% (w/w), or from 5% to 10% (w/w) of any other solid state forms or of a specified polymorphic form of Afatinib di-maleate.

As used herein, and unless stated otherwise, the term "anhydrous" in relation to crystalline Afatinib relates to crystalline Afatinib which does not include any crystalline water (or other solvents) in a defined, stoichiometric amount within the crystal. Moreover, an "anhydrous" form does not contain more than 1% (w/w) of either water or organic solvents as measured for example by TGA.

The term "solvate", as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount.

As used herein the term non-hygroscopic in relation to crystalline Afatinib refers to less than 0.2% (w/w) absorption of water at 25° C. and 80% RH, by the crystalline Afatinib as determined for example by TGA. Water can be for example atmospheric water.

As used herein, the term "reduced pressure" refers to a pressure of about 10 mbar to about 50 mbar.

As used herein, and unless indicated otherwise, the term "thermo-dynamical stability" in relation to solid state forms of Afatinib refers to resistance of the solid state form to polymorphic conversion under certain conditions, for example, heating, melting or dissolving. In some embodiments, the term refers to less than 20%, 10%, 5%, 1%, or 0.5% (w/w) conversion of crystalline Afatinib to any other solid state form of Afatinib as measured by PXRD. In some embodiments, the conversion is 1%-20%, 1%-10% or 1%-5% (w/w).

Depending on which other solid state forms comparison is made with, the solid state forms of Afatinib di-maleate of the present disclosure has advantageous properties selected from at least one of the following: chemical purity, flowability, solubility, dissolution rate, morphology or crystal habit, stability—such as chemical stability as well as thermal and mechanical stability with respect to polymorphic conversion, stability towards dehydration and/or storage stability, low content of residual solvent, a lower degree of hygroscopicity, flowability, and advantageous processing and handling characteristics such as compressibility, and bulk density.

A solid state form, such as a crystalline form or amorphous form, may be referred to herein as being characterized by graphical data "as depicted in" or "as substantially depicted in" a Figure. Such data include, for example, powder X-ray diffractograms and solid state NMR spectra. As is well-known in the art, the graphical data of the entire spectra or diffractogram potentially provides additional technical information to further define the respective solid state form (a so-called "fingerprint") which cannot necessarily be described by reference to numerical values or peak positions alone. In any event, the skilled person will understand that such graphical presentations of data may be subject to small variations, e.g., in peak relative intensities and peak positions due to certain factors such as, but not limited to, variations in instrument response and variations in sample concentration and purity, which are well known to the skilled person. Nonetheless, the skilled person would readily be capable of comparing the graphical data presented in the Figures provided herein with the graphical data generated for an unknown crystal form and confirm whether the two sets of graphical data are characterizing the same crystal form or two different crystal forms. A crystal form of a Afatinib di-maleate referred to herein as being characterized by graphical data "as depicted in" or "as substantially depicted in" a Figure will thus be understood to include any crystal forms of Afatinib di-maleate characterized with the graphical data having such small variations, as are well known to the skilled person, in comparison with the Figure.

As used herein, the term "isolated" in reference to solid state forms of Afatinib di-maleate of the present disclosure corresponds to a solid state form of Afatinib di-maleate that is physically separated from the reaction mixture in which it is formed.

As used herein, unless stated otherwise, the XRPD measurements are taken using copper Kα radiation wavelength 1.5418 Å.

A item, e.g., a reaction mixture, may be characterized herein as being at, or allowed to come to "room temperature" or "ambient temperature", often abbreviated as "RT." This means that the temperature of said item is close to, or the same as, that of the surrounding space, e.g., the room or fume hood, in which the item is located. Typically, room temperature is from about 20° C. to about 30° C., or about 22° C. to about 27° C., or about 25° C.

The amount of solvent employed in a chemical process, e.g., a reaction or crystallization, may be referred to herein as a number of "volumes" or "vol" or "V". For example, a material may be referred to as being suspended in 10 volumes (or 10 vol or 10V) of a solvent. In this context, this expression would be understood to mean milliliters of the solvent per gram of the material being suspended, such that suspending 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding solvent X (1.5 v/v) to a 100 ml reaction mixture would indicate that 150 mL of solvent X was added.

A process or step may be referred to herein as being carried out "overnight." This refers to a time interval, e.g., for the process or step, that spans the time during the night, when that process or step may not be actively observed. This time interval is from about 8 to about 20 hours, or about 10-18 hours, typically about 16 hours.

As used herein, the term "reduced pressure" refers to a pressure that is less than atmospheric pressure. For example, reduced pressure is about 10 mbar to about 50 mbar.

As used herein and as defined in WO2005/037824, crystalline Form A of Afatinib di-maleate is defined according to the X-ray powder reflections and intensities (standardized) of the 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline dimaleate as in the table below:

| 2·θ [°] | d-value [Å] | intensity I/I$_o$ [%] |
|---|---|---|
| 4.91 | 18.0 | 47 |
| 6.42 | 13.8 | 33 |
| 7.47 | 11.8 | 27 |
| 8.13 | 10.9 | 30 |
| 10.37 | 8.53 | 30 |
| 11.69 | 7.56 | 2 |
| 12.91 | 6.85 | 20 |
| 13.46 | 6.58 | 3 |
| 13.66 | 6.48 | 2 |
| 14.94 | 5.93 | 11 |
| 16.58 | 5.34 | 12 |
| 17.19 | 5.15 | 36 |
| 17.87 | 4.96 | 5 |
| 19.43 | 4.57 | 38 |
| 19.91 | 4.46 | 100 |
| 20.84 | 4.26 | 13 |
| 21.33 | 4.16 | 21 |
| 21.58 | 4.12 | 12 |
| 22.25 | 3.992 | 15 |
| 22.94 | 3.873 | 32 |
| 23.67 | 3.756 | 9 |
| 24.82 | 3.584 | 7 |
| 25.56 | 3.482 | 37 |
| 26.71 | 3.335 | 9 |
| 27.46 | 3.245 | 4 |
| 28.37 | 3.143 | 8 |
| 30.71 | 2.909 | 3 |
| 29.31 | 3.045 | 4 |
| 29.57 | 3.019 | 4 |
| 31.32 | 2.854 | 10 |
| 32.31 | 2.769 | 4 |
| 33.10 | 2.705 | 5 |
| 33.90 | 2.643 | 1 |
| 34.84 | 2.573 | 2 |
| 35.71 | 2.512 | 1 |
| 36.38 | 2.467 | 1 |
| 36.96 | 2.430 | 1 |
| 37.99 | 2.367 | 2 |
| 39.94 | 2.255 | 5 |

In one embodiment, the present disclosure relates to a crystalline form of Afatinib di-maleate, designated as form G, characterized by data selected from one or more of the following: X-ray powder diffraction pattern having peaks at 5.5, 9.0, 15.9, 17.1 and 22.6 degrees two theta±0.2 degrees two theta; an X-ray powder diffraction pattern as depicted in FIG. 1; and combinations of these data.

Figure 2:
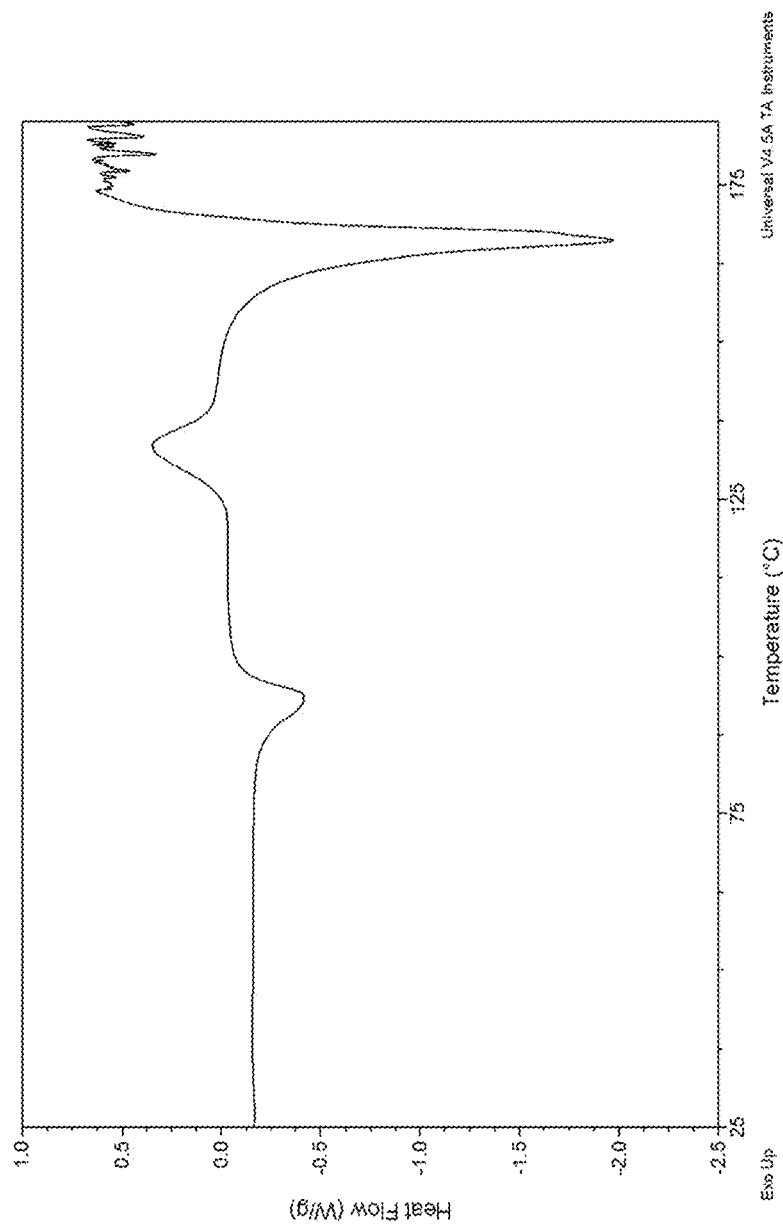
FIG. 2 shows a DSC thermogram of Afatinib di-maleate Form G.

Crystalline form G of Afatinib di-maleate may be further characterized by the X-ray powder diffraction pattern having peaks at 5.5, 9.0, 15.9, 17.1 and 22.6 degrees two theta ±0.2 degrees two theta and also having one, two, three, four or five additional peaks selected from: 9.4, 11.0, 19.3, 21.5 and 26.5±0.2 degrees two-theta; a DSC thermogram as depicted in FIG. 2; and combinations of these data.

Crystalline form G of Afatinib di-maleate may be characterized by each of the above characteristics alone and/or by all possible combinations, e.g. by X-ray powder diffraction pattern having peaks at 5.5, 9.0, 15.9, 17.1 and 22.6 degrees two theta±0.2 degrees two theta and by an X-ray powder diffraction pattern as depicted in FIG. 1.

Form G can be a hydrated form.

Figure 3:
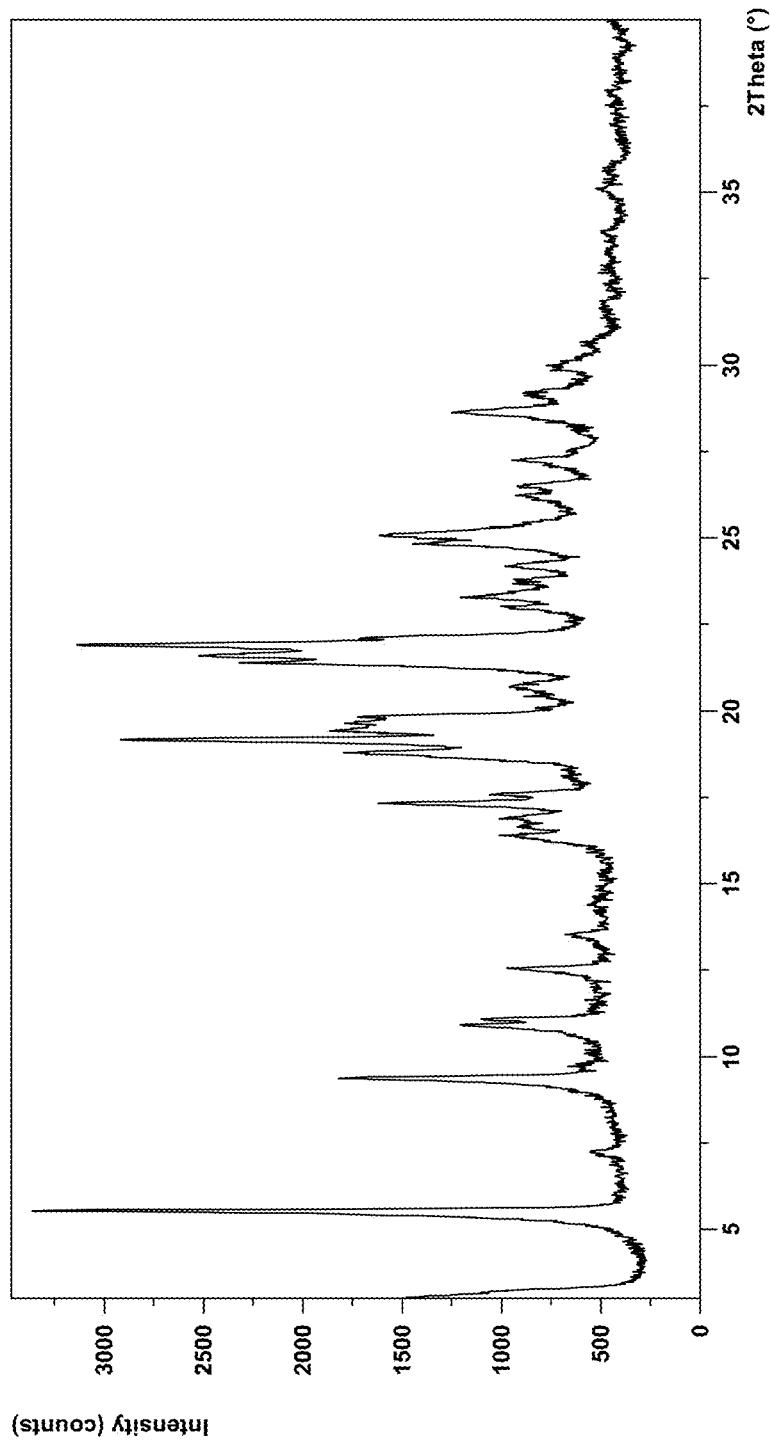
FIG. 3 shows an X-ray powder diffractogram of Afatinib di-maleate Form M.

In one embodiment, the present disclosure relates to a crystalline form of Afatinib di-maleate designated as form M, characterized by data selected from one or more of the following: X-ray powder diffraction pattern having peaks at 5.5, 10.9, 17.3, 21.9 and 25.1 degrees two theta±0.2 degrees two theta; an X-ray powder diffraction pattern as depicted in FIG. 3; a solid state $^{13}$C NMR spectrum with signals at about 170.1, 159.8, 111.1 and 97.8±0.2 ppm; a solid state $^{13}$C NMR spectrum as depicted in FIG. 13; and combinations of these data.

Alternatively, crystalline form M of Afatinib di-maleate may be characterized by data selected from one or more of the following: X-ray powder diffraction pattern having peaks at 5.5, 10.9, 12.6, 17.3, 21.9 and 25.1 degrees two theta±0.2 degrees two theta; an X-ray powder diffraction pattern as depicted in FIG. 3; a solid state $^{13}$C NMR spectrum with signals at about 170.1, 159.8, 111.1 and 97.8±0.2 ppm; a solid state $^{13}$C NMR spectrum as depicted in FIG. 13; and combinations of these data.

Figure 4:
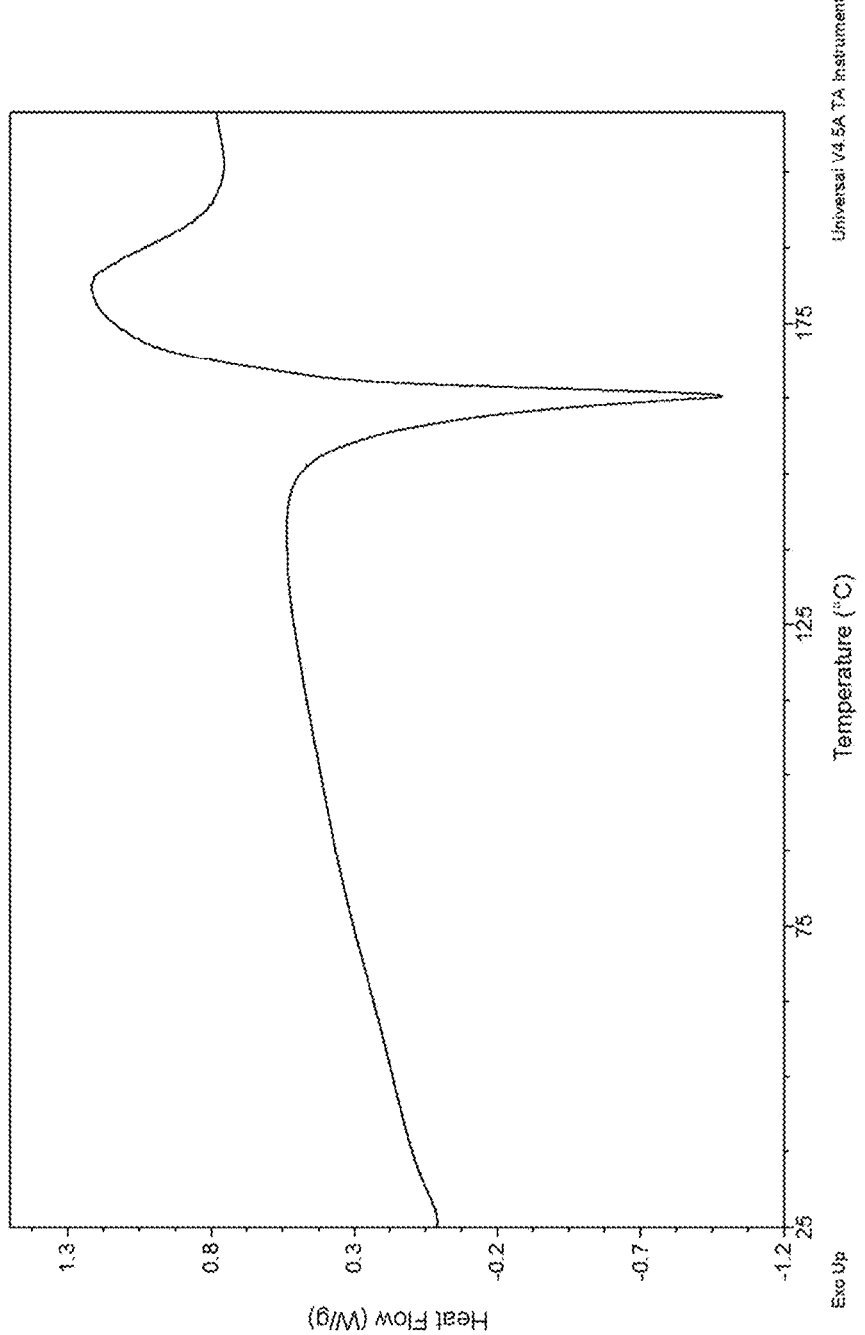
FIG. 4 shows a DSC thermogram of Afatinib di-maleate Form M.

Crystalline form M of Afatinib di-maleate may be further characterized by the X-ray powder diffraction pattern having peaks at 5.5, 10.9, 17.3, 21.9 and 25.1 degrees two theta ±0.2 degrees two theta and also having one, two, three, four or five additional peaks selected from: 7.3, 9.4, 16.4, 19.2 and 27.3 degrees two theta±0.2 degrees two-theta; a DSC thermogram as depicted in FIG. 4; a Raman spectrum having characteristic peaks at 1477, 1396, 1274, 1215 and 1198±4 cm$^{-1}$; a Raman spectrum substantially as depicted in FIG. 14; and combinations of these data.

Alternatively, crystalline form M of Afatinib di-maleate may be further characterized by the X-ray powder diffraction pattern having peaks at 5.5, 10.9, 12.6, 17.3, 21.9 and 25.1 degrees two theta±0.2 degrees two theta and also having one, two, three, four or five additional peaks selected from: 7.3, 9.4, 16.4, 19.2 and 27.3 degrees two theta±0.2 degrees two-theta; a DSC thermogram as depicted in FIG. 4; a Raman spectrum having characteristic peaks at 1477, 1396, 1274, 1215 and 1198±4 cm$^{-1}$; a Raman spectrum substantially as depicted in FIG. 14; and combinations of these data.

Crystalline form M of Afatinib di-maleate may be characterized by each of the above characteristics alone and/or by all possible combinations, e.g. by X-ray powder diffraction pattern having peaks at 5.5, 10.9, 17.3, 21.9 and 25.1 degrees two theta±0.2 degrees two theta and by an X-ray powder diffraction pattern as depicted in FIG. 3.

Form M can be an anhydrous form.

As discussed above, crystalline form M of Afatinib di-maleate has advantages. For example, crystalline form M may exhibit good polymorphic stability, e.g., when exposed to mechanical stress, it remains it's crystalline state. In particular, crystalline Form M of Afatinib di-maleate exhibits enhanced polymorphic stability compared to Form A of Afatinib di-maleate. As formulation processes often involve mechanical stress exerting technologies e.g. during grinding or under strong pressure in a tabletting machine, the polymorphic stability of API material is a desirable property.

In one embodiment, the present disclosure relates to a crystalline form of Afatinib di-maleate designated as form N, characterized by data selected from one or more of the following: X-ray powder diffraction pattern having peaks at 5.2, 5.4, 15.7, 21.1 and 27.4 degrees two theta±0.2 degrees two theta; an X-ray powder diffraction pattern as depicted in FIG. 5; a solid state $^{13}$C NMR spectrum with signals at about 156.1, 135.1, 107.1 and 57.4±0.2 ppm; a solid state $^{13}$C NMR spectrum as depicted in FIG. 15; and combinations of these data.

Figure 6:
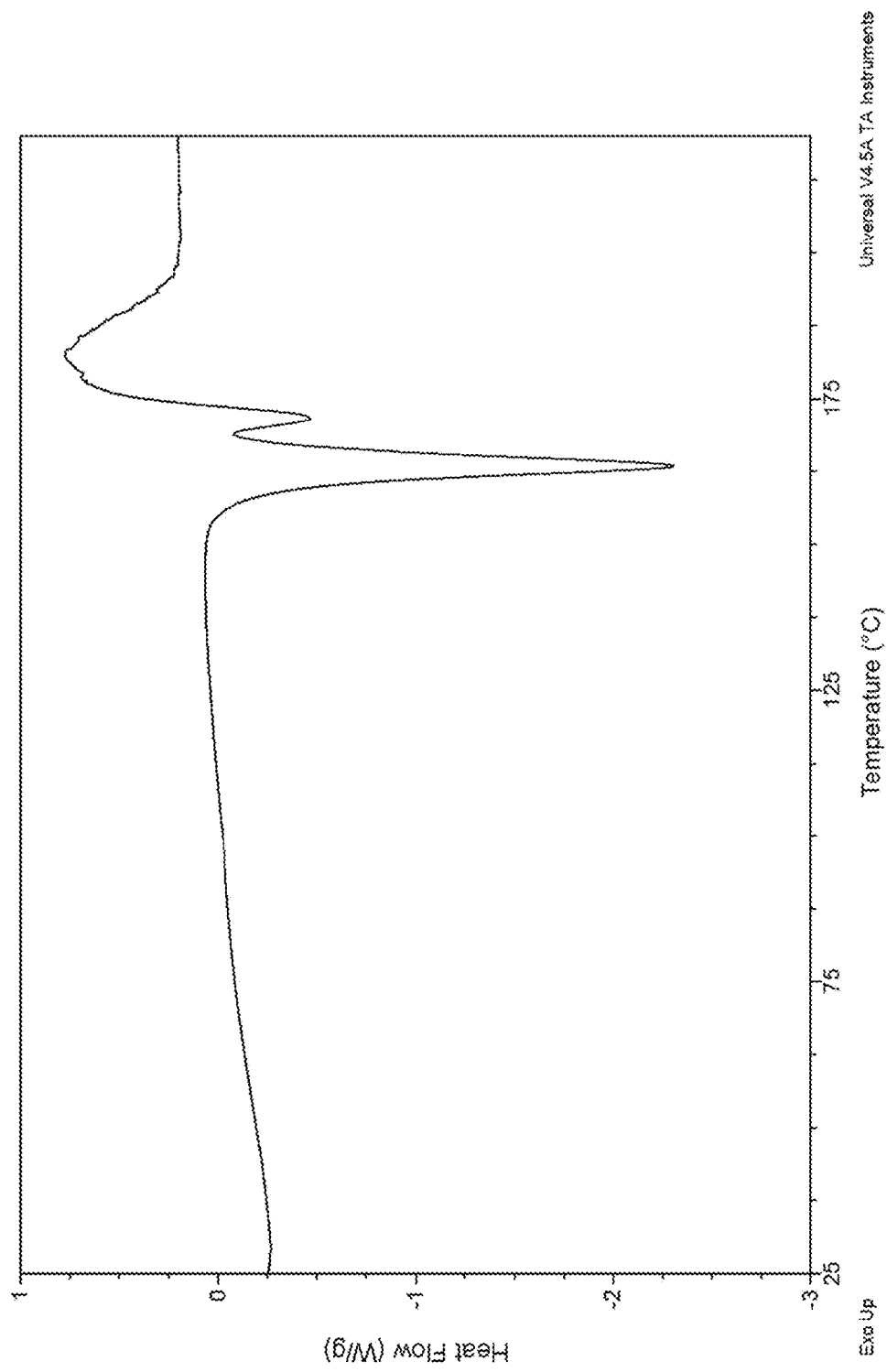
FIG. 6 shows a DSC thermogram of Afatinib di-maleate Form N.

Crystalline form N of Afatinib di-maleate may be further characterized by the X-ray powder diffraction pattern having peaks at 5.2, 5.4, 15.7, 21.1 and 27.4 degrees two theta±0.2 degrees two theta and also having one, two, three, four or five additional peaks selected from: 8.8, 13.3, 15.3, 22.7 and 27.9 degrees two theta±0.2 degrees two-theta; a DSC thermogram as depicted in FIG. 6; a Raman spectrum having characteristic peaks at 1529, 1459, 1367, 1307 and 1190±4 cm$^{-1}$; a Raman spectrum substantially as depicted in FIG. 16; and combinations of these data.

Alternatively, crystalline form N of Afatinib di-maleate may be further characterized by the X-ray powder diffraction pattern having peaks at 5.2, 5.4, 15.7, 21.1 and 27.4 degrees two theta±0.2 degrees two theta and also having one, two, three, four or five additional peaks selected from: 5.9, 8.8, 13.3, 15.3, 22.7 and 27.9 degrees two theta±0.2 degrees two-theta; a DSC thermogram as depicted in FIG. 6; a Raman spectrum having characteristic peaks at 1529, 1459, 1367, 1307 and 1190±4 cm$^{-1}$; a Raman spectrum substantially as depicted in FIG. 16; and combinations of these data.

Figure 5:
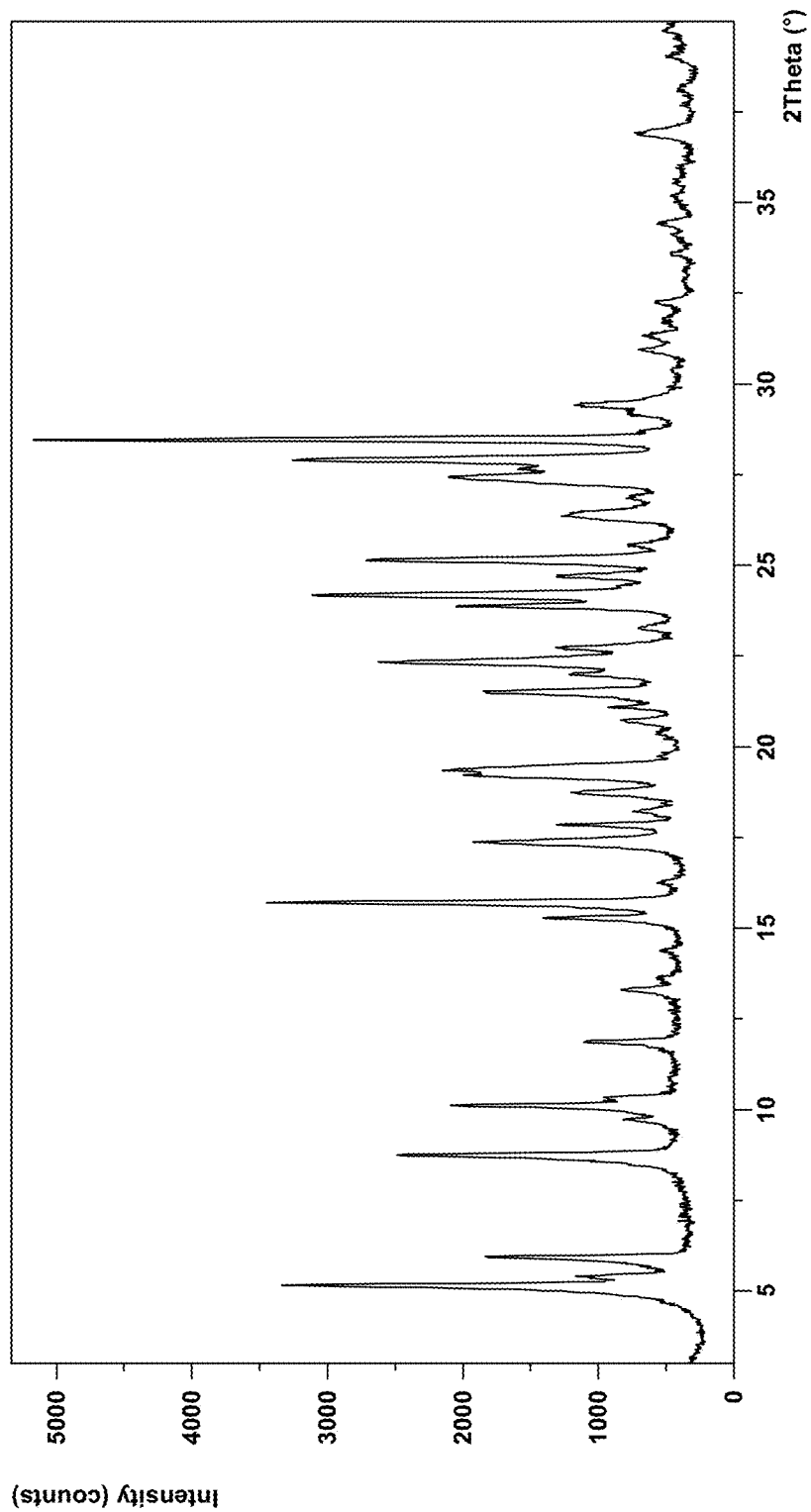
FIG. 5 shows an X-ray powder diffractogram of Afatinib di-maleate Form N.

Crystalline form N of Afatinib di-maleate may be characterized by each of the above characteristics alone and/or by all possible combinations, e.g. by X-ray powder diffraction pattern having peaks at 5.2, 5.4, 15.7, 21.1 and 27.4 degrees two theta±0.2 degrees two theta and by an X-ray powder diffraction pattern as depicted in FIG. 5.

Form N can be an anhydrous form.

As discussed above, crystalline form N of Afatinib di-maleate has some advantages. For example, crystalline form N may exhibit good wettability properties. Wetting is the ability of a liquid (e.g. water) to maintain contact with a solid surface (e.g., API). It is a precursor to dissolution and so the wettability of a drug particle has a significant influence on the dissolution rates and the release characteristics in an oral pharmaceutical delivery. Wettability may also influence the interactions with other particles during formulation and manufacture. A polymorph with enhanced wettability ensures proper solubility measurement of the API per se and in formulation during dissolution experiments, i.e., better distribution of water and properly wetted sample. Form N of Afatinib di-maleate exhibits better wettability over form A.

In one embodiment, the present disclosure relates to a crystalline form of Afatinib di-maleate designated as form Alpha, characterized by data selected from one or more of the following: X-ray powder diffraction pattern having peaks at 6.6, 10.6, 15.3, 16.3 and 24.2 degrees two theta±0.2 degrees two theta; an X-ray powder diffraction pattern as depicted in FIG. 7; a solid state $^{13}$C NMR spectrum with signals at about 171.6, 129.6, 102.4 and 79.0±0.2 ppm; a solid state $^{13}$C NMR spectrum as depicted in FIG. 17; and combinations of these data.

Figure 8:
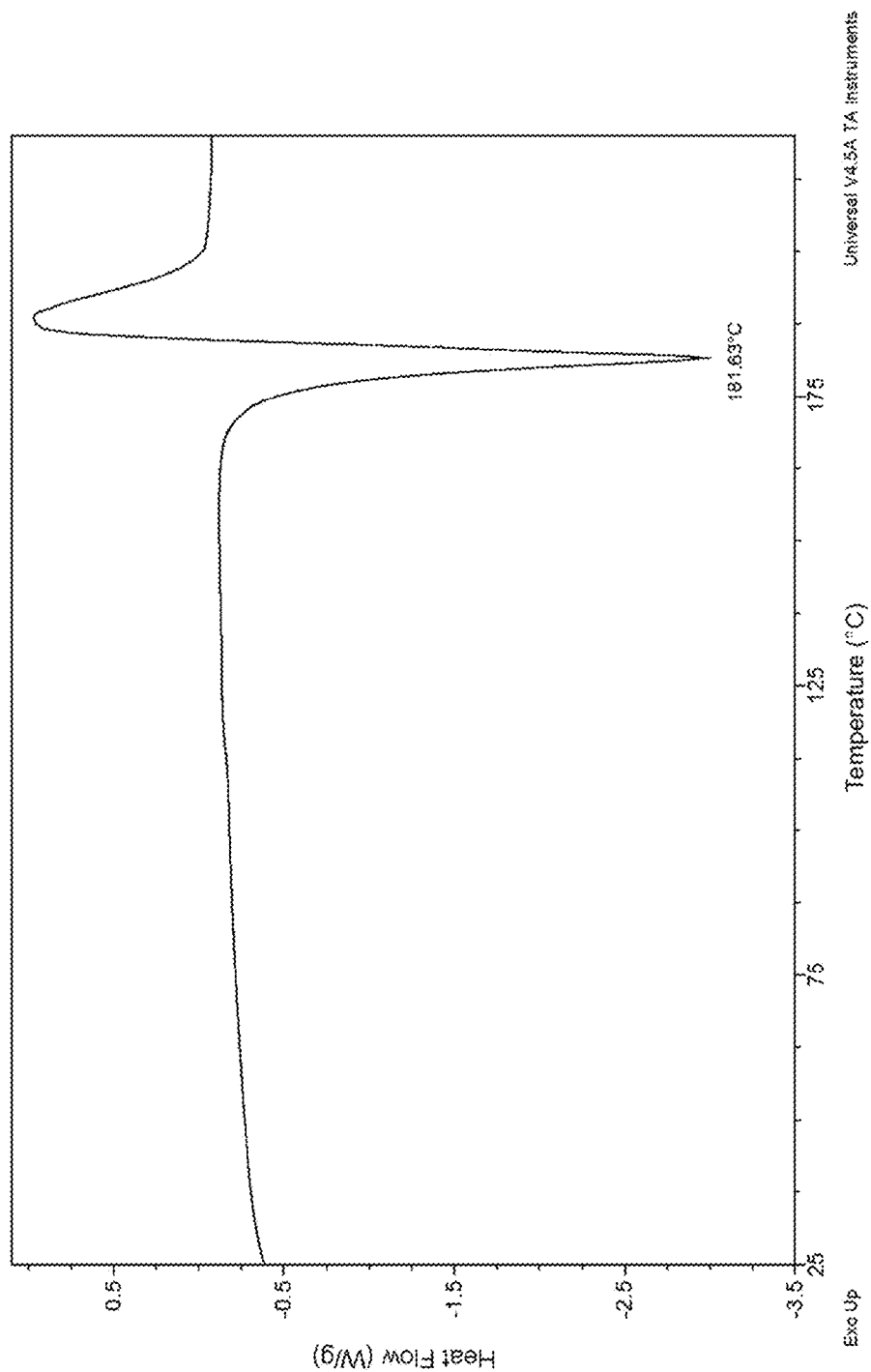
FIG. 8 shows a DSC thermogram of Afatinib di-maleate Form alpha.

Crystalline form Alpha of Afatinib di-maleate may be further characterized by the X-ray powder diffraction pattern having peaks at 6.6, 10.6, 15.3, 16.3 and 24.2 degrees two theta±0.2 degrees two theta and also having one, two, three, four or five additional peaks selected from: 13.3, 13.8, 17.0, 17.3 and 27.1 degrees two theta±0.2 degrees two-theta; a DSC thermogram as depicted in FIG. 8; a Raman spectrum having characteristic peaks at 3041, 1686, 1390, 1234 and 602±4 cm$^{-1}$; a Raman spectrum substantially as depicted in FIG. 18; and combinations of these data.

Figure 7:
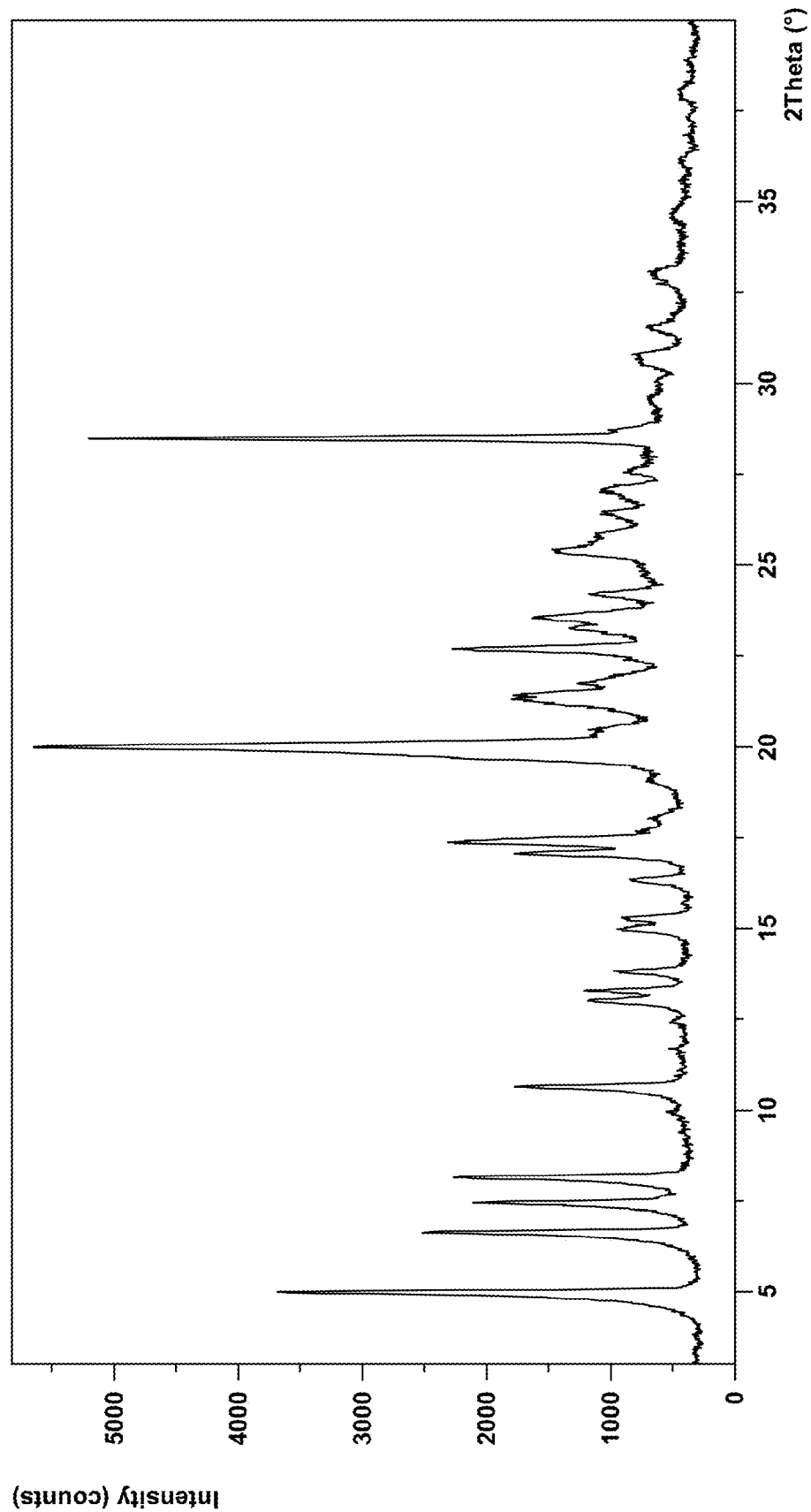
FIG. 7 shows an X-ray powder diffractogram of Afatinib di-maleate Form alpha.

Crystalline form Alpha of Afatinib di-maleate may be characterized by each of the above characteristics alone and/or by all possible combinations, e.g. by X-ray powder diffraction pattern having peaks at 6.6, 10.6, 15.3, 16.3 and 24.2 degrees two theta±0.2 degrees two theta and by an X-ray powder diffraction pattern as depicted in FIG. 7.

Form Alpha can be an anhydrous form.

As discussed above, crystalline form Alpha of Afatinib di-maleate has some advantages. For example, Afatinib dimaleate Form Alpha exhibits good thermodynamic stability. Pharmaceutical molecules may display solid to solid phase transformations, transformations between polymorphs or between unsolvated and solvated form, which may be detected by competitive slurry experiments. A competitive slurry experiment comparing thermodynamic stabilities of forms A and Alpha in ethanol at room temperature (e.g. after about 67 hours) resulted in pure form Alpha, which indicates an enhanced thermodynamic stability of form Alpha over form A.

In one embodiment, the present disclosure relates to a crystalline form of Afatinib di-maleate designated as form P, characterized by data selected from one or more of the following: X-ray powder diffraction pattern having peaks at 9.8, 10.8, 16.2, 18.4 and 20.4 degrees two theta±0.2 degrees two theta; an X-ray powder diffraction pattern as depicted in FIG. 9; and combinations of these data.

Figure 10:
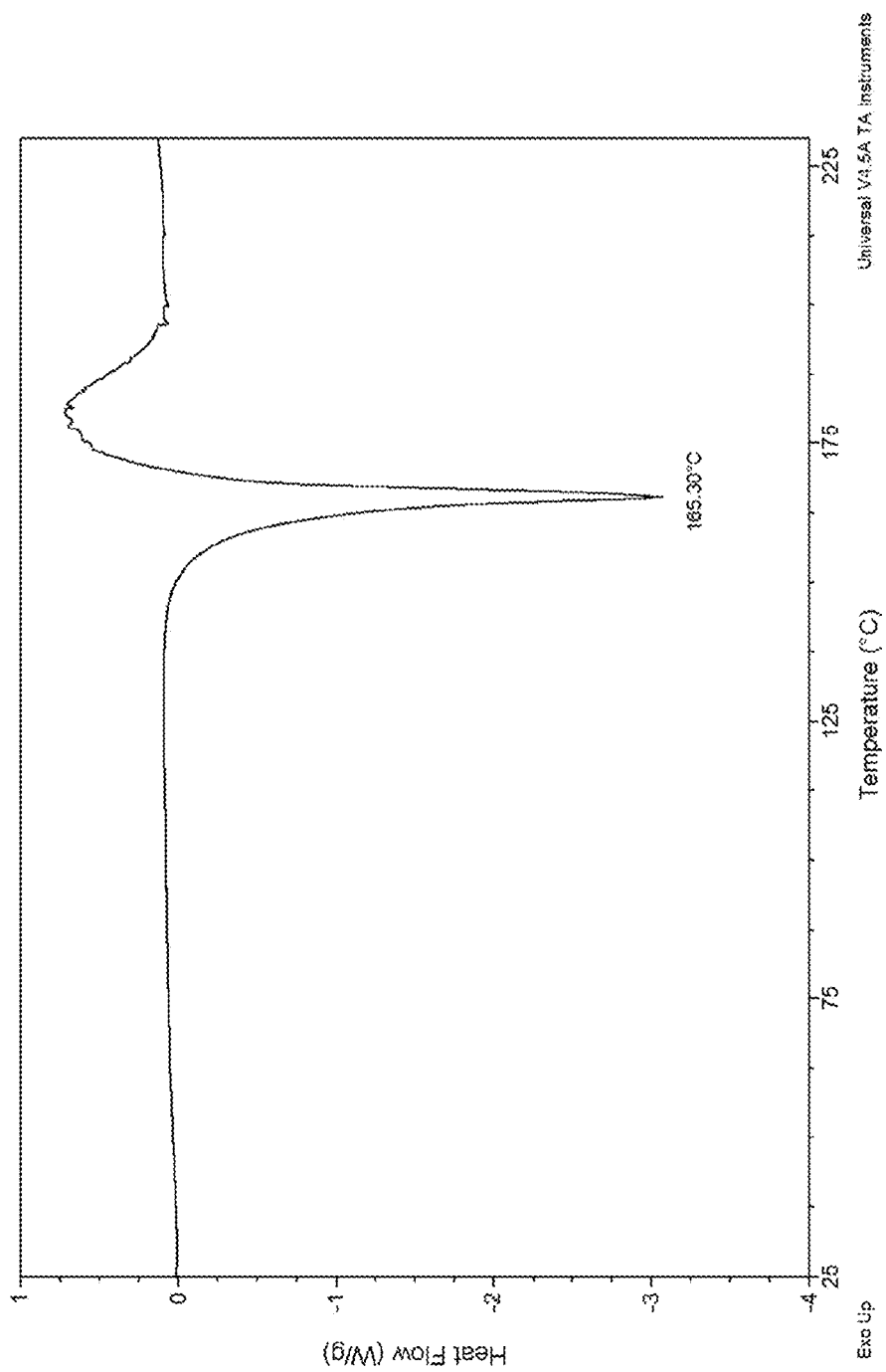
FIG. 10 shows a DSC thermogram of Afatinib di-maleate Form P.

Crystalline form P of Afatinib di-maleate may be further characterized by the X-ray powder diffraction pattern having peaks at 9.8, 10.8, 16.2, 18.4 and 20.4 degrees two theta±0.2 degrees two theta and also having one, two, three, four or five additional peaks selected from: 5.2, 18.7, 21.1, 23.9 and 26.0 degrees two theta±0.2 degrees two-theta; a DSC thermogram as depicted in FIG. 10; and combinations of these data.

Figure 9:
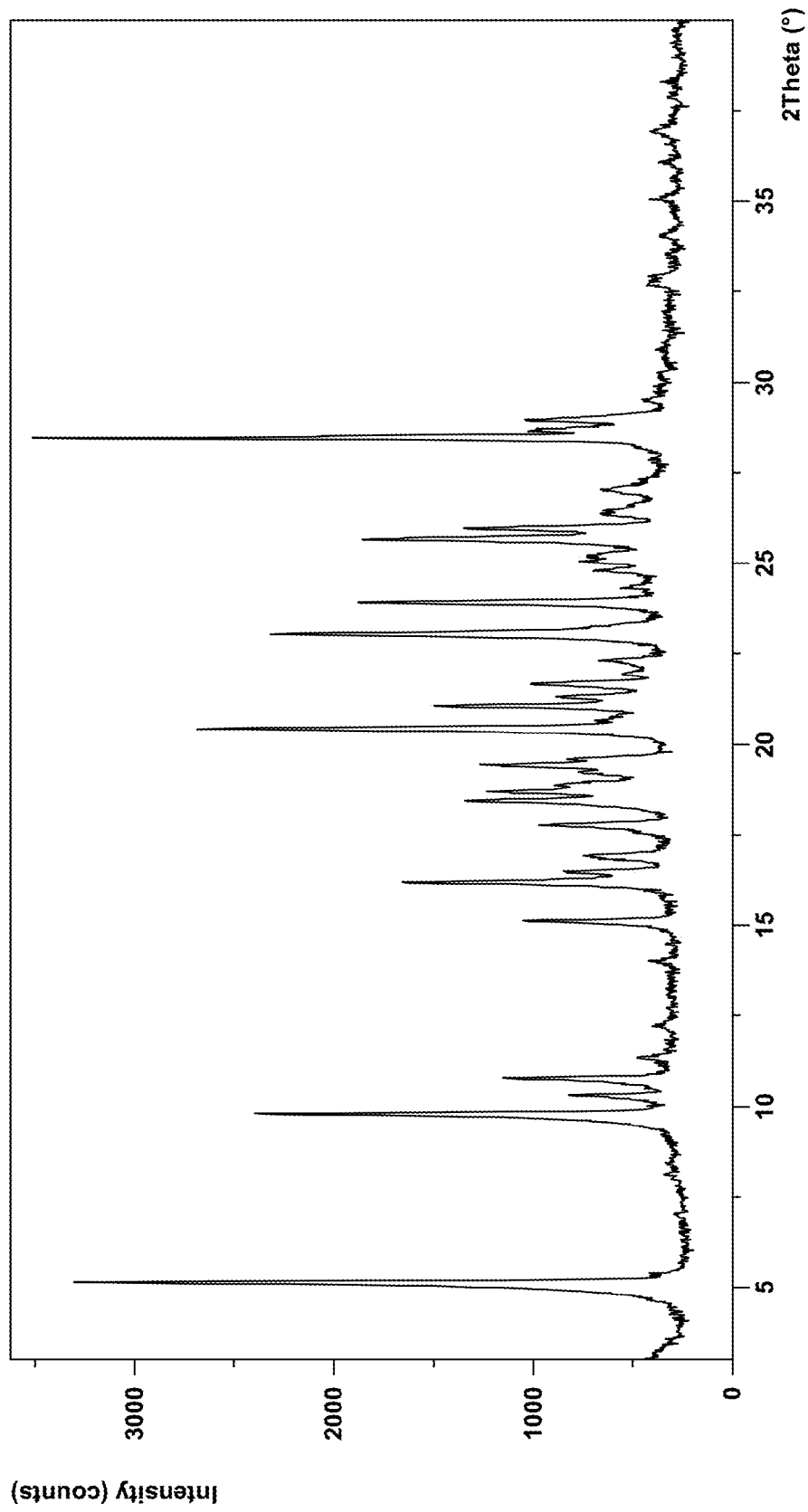
FIG. 9 shows an X-ray powder diffractogram of Afatinib di-maleate Form P.

Crystalline form P of Afatinib di-maleate may be characterized by each of the above characteristics alone and/or by all possible combinations, e.g. by X-ray powder diffraction pattern having peaks at 9.8, 10.8, 16.2, 18.4 and 20.4 degrees two theta±0.2 degrees two theta and by an X-ray powder diffraction pattern as depicted in FIG. 9.

Form P can be an anhydrous form.

The present disclosure further describes solid state form of Afatinib base.

The present disclosure further describes a crystalline form of Afatinib base designated form beta, characterized by data selected from one or more of the following: X-ray powder diffraction pattern having peaks at 6.6, 7.9, 9.1, 10.6 and 19.8 degrees two theta±0.2 degrees two theta; an X-ray powder diffraction pattern as depicted in FIG. 11; and combinations of these data.

Figure 12:
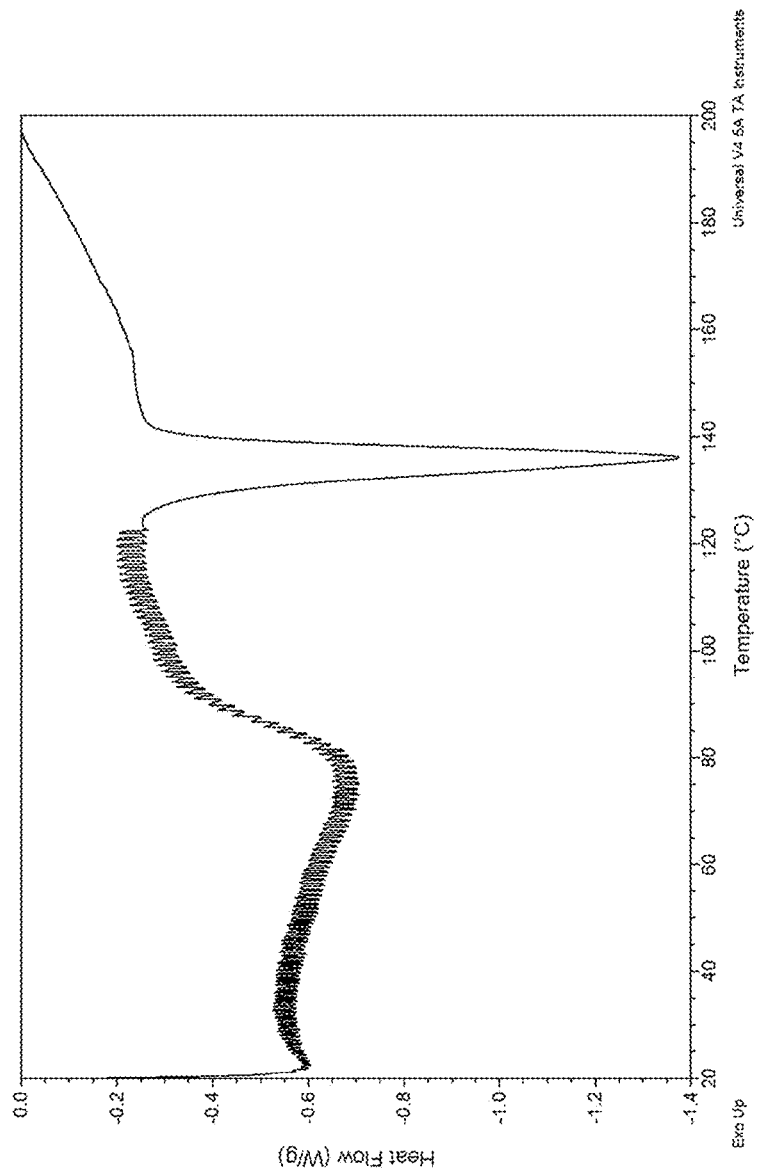
FIG. 12 shows a DSC thermogram of Afatinib base Form beta.

Crystalline form beta of Afatinib base may be further characterized by the X-ray powder diffraction pattern having peaks at 6.6, 7.9, 9.1, 10.6 and 19.8 degrees two theta±0.2 degrees two theta and also having one, two, three, four or five additional peaks selected from: 4.0, 15.2, 17.9, 22.1 and 24.4 degrees two theta±0.2 degrees two-theta; a DSC thermogram as depicted in FIG. 12; and combinations of these data.

Figure 11:
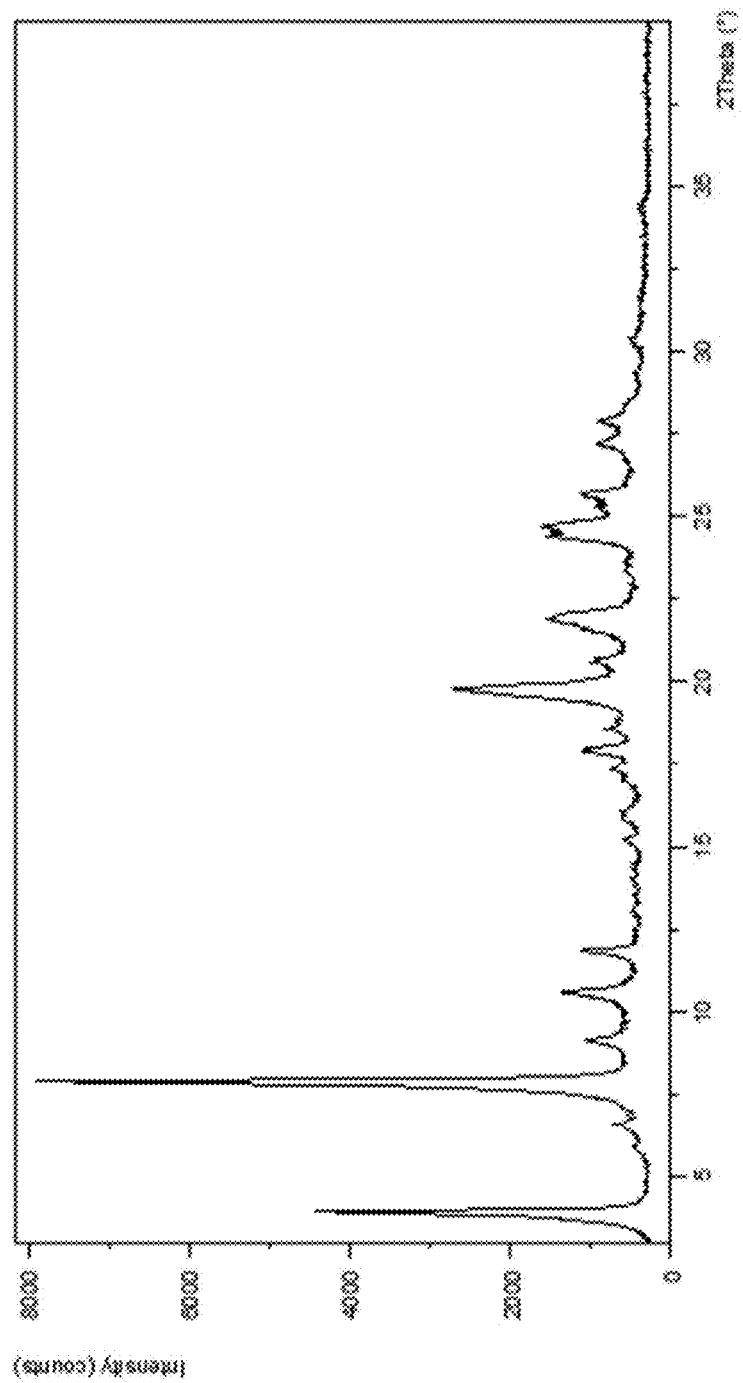
FIG. 11 shows a an X-ray powder diffractogram of Afatinib base Form beta.

Crystalline form beta of Afatinib base may be characterized by each of the above characteristics alone and/or by all possible combinations, e.g. by X-ray powder diffraction pattern having peaks at 6.6, 7.9, 9.1, 10.6 and 19.8 degrees two theta±0.2 degrees two theta and by an X-ray powder diffraction pattern as depicted in FIG. 11.

The above described crystalline Afatinib base can be used to prepare Afatinib salts and solid state forms thereof, particularly Afatinib di-maleate and solid state forms thereof.

The present disclosure also encompasses the use of the above Afatinib di-maleate forms of the present disclosure for the preparation of other Afatinib salts, or of Afatinib base, solid state forms and/or pharmaceutical compositions thereof.

The present disclosure further encompasses a process for preparing Afatinib or Afatinib salt comprising preparing any one or a combination of the above solid state forms of Afatinib di-maleate and converting it to Afatinib or Afatinib salt. The conversion can be done, for example, by basifying Afatinib di-maleate, i.e contacting it with a suitable base, to obtain Afatinib base, and optionally reacting Afatinib base with a suitable acid to obtain the corresponding acid addition salt.

The present disclosure also encompasses the use of the above Afatinib di-maleate solid state forms of the present disclosure for the preparation of pharmaceutical compositions of Afatinib di-maleate.

The present disclosure also encompasses the use of the above solid state forms of Afatinib di-maleate according to the disclosure in the preparation of pharmaceutical compositions.

The present disclosure comprises pharmaceutical compositions comprising the above forms of Afatinib di-maleate. Typically, the pharmaceutical composition is a solid composition and the Afatinib di-maleate retains its solid state form.

The pharmaceutical compositions can be prepared by a process comprising combining the above forms of Afatinib di-maleate of the disclosure with at least one pharmaceutically acceptable excipient.

The above forms of Afatinib di-maleate of the disclosure, and pharmaceutical compositions comprising said forms can also be used as a medicament.

The present disclosure further encompasses 1) the use of the above forms of Afatinib di-maleate according to the disclosure in the manufacture of a pharmaceutical composition, and 2) a method of treating a subject suffering from non-small cell lung cancer (NSCLC), or otherwise in need of the treatment, comprising administration of an effective amount of a pharmaceutical composition comprising said forms of Afatinib di-maleate according to the disclosure.

Having thus described the disclosure with reference to particular preferred embodiments and illustrative examples, those in the art will appreciate modifications to the disclosure as described and illustrated that do not depart from the spirit and scope of the disclosure as disclosed in the specification. The Examples are set forth as an aid in understanding the disclosure but are not intended to, and should not be construed to limit its scope in any way.

XRPD Method:

Sample after being powdered in a mortar and pestle is applied directly on a silicon plate holder. The X-ray powder diffraction pattern was measured with Philips X'Pert PRO X-ray powder diffractometer, equipped with Cu irradiation source=1.54184 Å (Ångström), X'Celerator (2.022° 2θ) detector. Scanning parameters: angle range: 3-40 deg., step size 0.0167, time per step 37 s, continuous scan. The described peak positions were determined using silicon powder as an internal standard in an admixture with the sample measured. The position of the silicon (Si) peak was corrected to silicone theoretical peak: 28.45 degrees two theta and the positions of the measured peaks were corrected respectively.

DSC Method:

DSC analysis was performed on Q1000 MDSC (TA instruments) with heating rate of 10° C./min, under nitrogen flow of 50 ml/min. A hermetic aluminium, closed pan with hole was used, and the sample mass was about 1-5 mg.

Solid State NMR Method:

Solid-state $^{13}$C NMR spectra were recorded with variable amplitude cross polarization, magic angle spinning and high power proton decoupling using a BRUKER Avance II+ spectrometer operating at 125 MHz and ambient temperature (about 25° C.—not controlled). A probe using 4 mm o.d. zirconia rotors was employed. The operation conditions were: contact time: 2 ms; recycle delay: 2 s 1024 scans; spin rate of 11 kHz. Chemical shifts were referenced via a replacement sample of glycine (carboxyl carbon chemical shift assigned as 176.03 ppm relative to the signal of tetramethylsilane).

FT-Raman Spectroscopy Method:

Raman spectra were acquired on a Nicolet 6700 interferometer, equipped with an NXR FT-Raman modul. Nd-YAG laser (1064 nm, 500 mW) was used to excite the sample. The spectrometer utilizes a CaF2 beamsplitter and a liquid nitrogen cooled Ge detector. The spectra were recorded at resolution of 4 cm−1.

EXAMPLES

Example 1A

Preparation of the Afatinib Base Starting Material

The starting material Afatinib base can be prepared according to the following process:

Step a: Preparation of (S)-N-(3-chloro-4-fluorophenyl)-6-nitro-7-(tetrahydrofuran-3-yloxy)quinazolin-4-amine To the suspension of 94.0 g of potassium tert-butoxide in 405.0 ml of DMF at −10° C. to −5° C., 75.0 g of (S)-tetrahydrofuran-3-ol was added slowly. The suspension was stirred for 1 hour at −10° C. to 0° C. when 70.0 g of N-(3-chloro-4-fluorophenyl)-7-fluoro-6-nitroquinazolin-4-amine in small portions at −10° C. to 3° C. was added. After addition, the reaction mixture was heated to 20° C.-25° C. and stirred for 1 hour. To the reaction mixture, 2010 ml of water was added at 20° C.-25° C. dropwise, pH value was adjusted to about 9.5 with 5 M HCl (aq), and stirred for 1 hour at 20° C.-25° C. Crystals were filtered off, washed with 225.0 ml of water and dried at 70° C./15 mbar for 16 hours. Obtained crystals of (S)-N-(3-chloro-4-fluorophenyl)-6-nitro-7-(tetrahydrofuran-3-yloxy)quinazolin-4-amine were recrystallized from acetone. 68.4 g of (S)-N-(3-chloro-4-fluorophenyl)-6-nitro-7-(tetrahydrofuran-3-yloxy)quinazolin-4-amine was obtained.

Step b: Preparation of (S)-$N^4$-(3-chloro-4-fluorophenyl)-7-(tetrahydrofuran-3-yloxy)quinazoline-4,6-diamine 67.4 g of (S)-N-(3-chloro-4-fluorophenyl)-6-nitro-7-(tetrahydrofuran-3-yloxy)quinazolin-4-amine (prepared according to step a) was hydrogenated in 269 ml of DMF in the presence of 22.4 g of Raney-Nickel and 12.8 g of NH$_4$Cl at 40° C./7 bar for about 44 hours. The catalyst was filtered off, washed with small amount of DMF and the filtrate was added dropwise at 20° C.-25° C. to 943.0 ml of water. The suspension was stirred for 1.5 hours at 20° C.-25° C., cooled down to 0° C.-5° C. and stirred for 16.5 hours. Crystals were filtered off, washed four times with 50.0 ml of water and dried at 40° C.-50° C. for about 56 hours. Obtained crystals of (S)-$N^4$-(3-chloro-4-fluorophenyl)-7-(tetrahydrofuran-3-yloxy)quinazoline-4,6-diamine were treated with charcoal and recrystallized twice from the acetone/methanol. 40.7 g of (S)-$N^4$-(3-chloro-4-fluorophenyl)-7-(tetrahydrofuran-3-yloxy)quinazoline-4,6-diamine was obtained.

Step c: Preparation of S)-diethyl 2-(4-(3-chloro-4-fluorophenylamino)-7-(tetrahydrofuran-3-yloxy) quinazolin-6-ylamino)-2-oxoethylphosphonate To the suspension of 28.0 g of 1,1'-carbonyldiimidazole in 98.0 ml of THF at about 40° C., a solution of 33.9 g of 2-(diethoxyphosphoryl)acetic acid in 50.6 ml of THF was added dropwise. The reaction mixture was stirred for 1 hour at about 40° C. and then added to the solution of 40.5 g of (S)-$N^4$-(3-chloro-4-fluorophenyl)-7-(tetrahydrofuran-3-yloxy)quinazoline-4,6-diamine (prepared according to step b) in 168 ml of THF at about 40° C. dropwise. The reaction mixture was cooled down to about 30° C. and stirred for 2.4 h hours when 405.0 ml of MTBE was added dropwise. The reaction mixture was cooled down to about 20° C. and stirred for 1.5 hours. Crystals were filtered off, washed twice with 40.5 ml of THF/MTBE 1:1, once with 40.5 ml of water and dried at 50° C./15 mbar for about 16 hours. 41.0 g of (S)-diethyl 2-(4-(3-chloro-4-fluorophenylamino)-7-(tetrahydrofuran-3-yloxy)quinazolin-6-ylamino)-2-oxoethylphosphonate was obtained.

Step d: Preparation of 2-(dimethylamino)-1-hydroxyethanesulfonic acid

To the solution of 45.2 ml of conc. HCl (aq) and 25.1 ml of water at 20° C.-25° C., 50.0 g of 2,2-diethoxy-N,N-dimethylethanamine was added dropwise. After stirring for 2.5 hours at about 40° C., solution of 53.1 g of Na$_2$S$_2$O$_5$ in 89.0 ml of water was added dropwise at about 40° C. The reaction mixture was stirred for 1 hour at 40° C. when 251 ml of ethanol was added. The suspension was cooled down to 0° C.-5° C. and stirred for 1.5 hours. Crystals were filtered off, washed with 100.0 ml of ethanol and dried at 45° C./15 mbar for about 17 hours. 48.0 g of 2-(dimethylamino)-1-hydroxyethanesulfonic acid was obtained.

Step e: Preparation of (S,E)-N-(4-(3-chloro-4-fluorophenylamino)-7-(tetrahydrofuran-3-yloxy)quinazolin-6-yl)-4-(dimethylamino)but-2-enamide (Afatinib Base)

40.8 g of (S)-diethyl 2-(4-(3-chloro-4-fluorophenylamino)-7-(tetrahydrofuran-3-yloxy)quinazolin-6-ylamino)-2-oxoethylphosphonate (prepared according to step c) and 3.28 g of lithium chloride were suspended in 245 ml of ethanol and cooled down to −10° C.-0° C. To the suspension, 45.0 g of 45% KOH (aq) and then a solution of 19.6 g of 2-(dimethylamino)-1-hydroxyethanesulfonic acid (prepared according to step d) in 196 ml of water were added dropwise. After stirring for 3 hours at −10° C.-0° C., to the suspension 245 ml of water was added and stirred further at −10° C.-0° C. for 1.5 hours. Crystals were filtered off, washed thrice with 70.0 ml of water and dried at 50° C./15 mbar for about 16 hours. 33.3 g of (S,E)-N-(4-(3-chloro-4-fluorophenylamino)-7-(tetrahydrofuran-3-yloxy)quinazolin-6-yl)-4-(dimethylamino)but-2-enamide was obtained (Afatinib base form beta).

Example 1B

Preparation of the Afatinib Base Starting Material

The starting material Afatinib base can be prepared according to the following alternative process:

Step a: Preparation of (S)-N-(3-chloro-4-fluorophenyl)-6-nitro-7-(tetrahydrofuran-3-yloxy)quinazolin-4-amine To a suspension of 94.0 g of potassium tert-butoxide in 405.0 ml of DMF at −10° C. to −5° C., 75.0 g of (S)-tetrahydrofuran-3-ol was added slowly. The suspension was stirred for 1 hour at −10° C. to 0° C. and then 70.0 g of N-(3-chloro-4-fluorophenyl)-7-fluoro-6-nitroquinazolin-4-amine in small portions at −10° C. to 8° C. was added. After addition, the reaction mixture was heated at 20° C.-25° C. and stirred for 1 hour. Obtained reaction mixture was added dropwise to 2010 ml of water at 20° C.-25° C., pH value was adjusted to about 9.5 with 5 M HCl (aq), and stirred for 1 hour at 20-25° C. Crystals were filtered off, washed with 225.0 ml of water and dried at 70° C./vacuum for 24 hours.

86.2 g of crystals of (S)-N-(3-chloro-4-fluorophenyl)-6-nitro-7-(tetrahydrofuran-3-yloxy)quinazolin-4-amine were obtained.

Step b: Preparation of (S)-N$^4$-(3-chloro-4-fluorophenyl)-7-(tetrahydrofuran-3-yloxy)quinazoline-4,6-diamine 75.0 g of (S)-N-(3-chloro-4-fluorophenyl)-6-nitro-7-(tetrahydrofuran-3-yloxy)quinazolin-4-amine was hydrogenated in 300 ml of DMF in the presence of 25.0 g of Raney-Nickel and 14.3 g of NH$_4$Cl at 40° C./7 bar for about 54 hours. The catalyst was filtered off, washed with small amount of DMF and the filtrate was added dropwise at 20° C.-25° C. to 1050 ml of water. The suspension was cooled down to 0° C.-5° C. and stirred for 2.5 hours. Crystals were filtered off, washed three times with 50.0 ml of water and dried at 60° C./vacuum for 18 hours. 57.1 g of crystals of (S)-N$^4$-(3-chloro-4-fluorophenyl)-7-(tetrahydrofuran-3-yloxy)quinazoline-4,6-diamine were obtained.

Step c: Preparation of (S)-diethyl 2-(4-(3-chloro-4-fluorophenylamino)-7-(tetrahydrofuran-3-yloxy)quinazolin-6-ylamino)-2-oxoethylphosphonate To a suspension of 31.5 g of 1,1'-carbonyldiimidazole in 110.0 ml of THF at about 40° C., a solution of 38.0 g of 2-(diethoxyphosphoryl)acetic acid in 57.0 ml of THF was added dropwise. The reaction mixture was stirred for 1 hour at about 40° C. and then added to the solution of 45.5 g of (S)-N$^4$-(3-chloro-4-fluorophenyl)-7-(tetrahydrofuran-3-yloxy)quinazoline-4,6-diamine (ZM-3106-15) in 189 ml of THF at about 40° C. dropwise. The reaction mixture was cooled down to about 30° C., stirred for 3 h hours and then 455.0 ml of MTBE was added dropwise. The reaction mixture was cooled down to about 20° C., crystals were filtered off, washed twice with 50.0 ml of THF/MTBE 1:1, once with 50.0 ml of water and dried at 60° C./vacuum for about 17 hours. 49.7 g of crystals of (S)-diethyl 2-(4-(3-chloro-4-fluorophenylamino)-7-(tetrahydrofuran-3-yloxy)quinazolin-6-ylamino)-2-oxoethylphosphonate were obtained.

Step d: Preparation of 2-(dimethylamino)-1-hydroxyethanesulfonic acid

To a solution of 36.2 ml of concentrated HCl (aq) and 20.0 ml of water at 20° C. -35° C., 40.0 g of 2,2-diethoxy-N,N-dimethylethanamine was added dropwise. After stirring for 2.5 hours at about 40° C., solution of 45.0 g of Na$_2$S$_2$O$_5$ in 71.0 ml of water was added dropwise at about 40° C. The reaction mixture was stirred for 1 hour at 40° C. and then 201 ml of ethanol was added. The suspension was cooled down to 0° C.-5° C. and stirred for 2 hours. Crystals were filtered off, washed with 100.0 ml of ethanol and dried at 45° C./vacuum for about 17 hours. 33.0 g of crystals of 2-(dimethylamino)-1-hydroxyethanesulfonic acid were obtained

Step e: Preparation of (S,E)-N-(4-(3-chloro-4-fluorophenylamino)-7-(tetrahydrofuran-3-yloxy)quinazolin-6-yl)-4-(dimethylamino)but-2-enamide (Afatinib base)

60.3 g of (S)-diethyl 2-(4-(3-chloro-4-fluorophenylamino)-7-(tetrahydrofuran-3-yloxy)quinazolin-6-ylamino)-2-oxoethylphosphonate and 4.85 g of lithium chloride were suspended in 362 ml of ethanol and cooled down to −10° C.-0° C. To the suspension, 66.3 g of 45% KOH (aq) and then a solution of 28.9 g of 2-(dimethylamino)-1-hydroxyethanesulfonic acid in 289 ml of water were added dropwise. After stirring for about 3 hours at −10-0° C., to the suspension 362 ml of water was added, crystals were filtered off, washed with 6×100.0 ml of water and dried at 50° C./vacuum for about 17 hours. 47.0 g of crystals of (S,E)-N-(4-(3-chloro-4-fluorophenylamino)-7-(tetrahydrofuran-3-yloxy)quinazolin-6-yl)-4-(dimethylamino)but-2-enamide were obtained (afatinib base).

2.50 g of afatinib base was recrystallized form i-butyl acetate/cyclohexane. 2.16 g of crystals of afatinib base were obtained.

Example 1C

Preparation of the Afatinib Base

The starting material Afatinib base can be prepared according to the following alternative process:

Step a: preparation of (S)-N-(3-chloro-4-fluorophenyl)-6-nitro-7-((tetrahydrofuran-3-yl)oxy)quinazolin-4-amine 50 g of potassium-tert-butoxide and 150 ml of dimethylformamide (DMF) were charged in 1 L reactor and reaction mixture was cooled at −5° C. 40.5 g of (S)-tetrahydrofuran-3-ol was added dropwise and reaction mixture was stirred for 30 minutes. 50 g of N-(3-chloro-4-fluorophenyl)-7-fluoro-6-nitroquinazolin-4-amine was added in few portions and reaction mixture was heated at 20-25° C. After reaction was finished (about 1 hour), 500 ml of water was added and product crystallized. Suspension was stirred for 1.5 hours. Crystals were filtered, washed with 150 ml DMF/water 1:4, 150 ml water and finally with 150 ml acetonitrile. Crystals were dried at 50° C. under reduced pressure to obtain 57.4 g of (S)-N-(3-chloro-4-fluorophenyl)-6-nitro-7-((tetrahydrofuran-3-yl)oxy)quinazolin-4-amine.

Step b: preparation of(S)-N4-(3-chloro-4-fluorophenyl)-7-((tetrahydrofuran-3-yl)oxy)quinazoline-4,6-diamine crude 70.0 g of (S)-N-(3-chloro-4-fluorophenyl)-6-nitro-7-((tetrahydrofuran-3-yl)oxy)quinazolin-4-amine prepared by example above, 23.1 g of Raney nickel catalyst, 13.3 g of ammonium chloride and 280 ml of dimethylformamide (DMF) was charged in 600 ml reactor for hydrogenation. Reaction mixture was hydrogenated at 5 bar pressure of hydrogen at 40° C. for 19 hours. After reaction was finished, catalyst was filtered and washed with 2×70 ml DMF. Filtrate and washing were combined and added dropwise in to 980 ml of water. Obtained suspension was stirred at 20-25° C. for 30 minutes, cooled at 0-5° C. and stirred for additional 2 hours. Crystals were filtered, washed with 105 ml water: DMF 3:1 mixture and 2 times with 105 ml of water. Crystals were dried at 50° C. under reduced pressure to obtain 60.4 g of (S)-N$^4$-(3-chloro-4-fluorophenyl)-7-((tetrahydrofuran-3-yl)oxy)quinazoline-4,6-diamine crude.

Step c: Recrystallization of (S)-N$^4$-(3-chloro-4-fluorophenyl)-7-((tetrahydrofuran-3-yl)oxy)quinazoline-4,6-diamine 59.5 g of (S)-N$^4$-(3-chloro-4-fluorophenyl)-7-((tetrahydrofuran-3-yl)oxy)quinazoline-4,6-diamine crude, prepared by example above and 429 ml acetone was charged in 1 L reactor and heated at reflux temperature. Solution was treated with charcoal for about 20 minutes. Charcoal was filtered off and washed with 16 ml of acetone. Filtrate and washing were combined and cooled down at 20-25° C. Thick suspension was formed. Suspension was stirred at 20-25° C. for 30 min, cooled at 0-5° C. and stirred for additional 2 hours. Crystals were filtered, washed with 2×53 ml cold acetone and dried at 50° C. under reduced pressure for 16 hours to obtain 40.8 g of (S)-N$^4$-(3-chloro-4-fluorophenyl)-7-((tetrahydrofuran-3-yl)oxy)quinazoline-4,6-diamine.

Step d: Preparation of Afatinib Base 32.0 g of (E)-4-(dimethylamino)but-2-enoic acid, 160 ml ethyl acetate and 1.2 ml DMF was charged in 1 L reactor. Suspension was cooled at −2° C. 21.5 g of oxalyl chloride was added over 5-10 minutes. Reaction mixture was heated to 20° C. and stirred for 1.5 hours. Solution of 50.0 g of (S)-N$^4$-(3-chloro-4-fluorophenyl)-7-((tetrahydrofuran-3-yl) oxy)quinazoline-4,6-diamine, prepared by example above in 250 ml NMP was added in suspension of (E)-4-(dimethylamino)but-2-enoyl chloride at temperatures below 18° C. After addition, reaction mixture was heated at 20-25° C. and stirred for about 1 hour. After reaction was completed, 300 ml of water and 200 ml of ethyl acetate was added. Layers were separated and ethyl acetate layer was extracted once more with 100 ml of water. Water layers were combined. 300 ml ethyl acetate was added and pH was adjusted to about 8.3-8.4 by addition of 40% NaOH. Layers were separated, water layer was extracted with 2×150 ml ethyl acetate. Organic layers were combined, washed with 2×250 ml water and evaporated to dryness.

Example 1C-C

Preparation of the Afatinib Base Form C

Residue on evaporation from example 1C was dissolved in 600 ml of iso-butyl acetate (i-BuOAc) by heating at 70° C. Solution crystallized by cooling at 45° C. Suspension was cooled at 0-5° C. and stirred for 16 hours. Crystals were filtered, washed with 100+50 ml cold i-BuOAc and dried at 50° C. under reduced pressure for 6 hours. 55.0 g of AFT base form C was obtained. The obtained product was analyzed by PXRD.

Example 2

Preparation of Afatinib Dimaleate Form G

To a solution of 0.500 g of afatinib base (prepared according to the procedure described in example 1A) in 10.0 ml acetone at about 50° C., solution of 0.245 g (2.05 eq) of 99% maleic acid in 2.50 ml acetone was added. Crystallization occurred at the end of the acid addition. Suspension was stirred for one hour at about 50° C., cooled to a room temperature (20° C.-25° C.), stirred for another hour and finally cooled to 0° C.-5° C. and stirred for about two hours. Crystals were filtered off, washed with 2.0 ml of acetone and dried at 40° C./15 mbar for about 17 hours. 0.650 g of crystals of afatinib di-maleate were obtained. The obtained product was analyzed by PXRD.

Example 3

Preparation of Afatinib Dimaleate Form G

To a solution of 0.500 g of afatinib base (prepared according to the procedure described in example 1A) in 10.0 ml of acetone/methanol 19:1 at 50° C.-55° C., solution of 0.245 g (2.05 eq) of 99% maleic acid in 2.50 ml acetone/methanol 19:1 was added. Crystallization occurred at the end of the acid addition. Suspension was stirred for one hour at 50° C.-55° C., cooled to a room temperature (20° C.-25° C.), stirred for another hour and finally cooled to 0° C.-5° C. and stirred for about one hour. Crystals were filtered off, washed with 2.0 ml of acetone/methanol 19:1 and dried at 50° C./15 mbar for about 17 hours. 0.670 g of crystalline afatinib di-maleate was obtained. The obtained product was analyzed by PXRD (FIG. 1).

Example 4

Preparation of Afatinib Dimaleate Form G

To a solution of 5.00 g of afatinib base (prepared according to the procedure described in example 1A) in 100.0 ml of acetone/methanol 19:1 at 50° C.-55° C., solution of 2.45 g (2.05 eq) of 99% maleic acid in 25.0 ml acetone/methanol 19:1 was added. During acid addition, solution was seeded with small amount of afatinib dimaleate of example 2. Obtained suspension was stirred for about one hour at 50° C.-55° C., cooled to a room temperature (20° C.-25° C.), stirred for about 1 hour and finally cooled to 0° C.-5° C. and stirred for about 1.5 hours. Crystals were filtered off, washed with 2×10.0 ml of acetone/methanol 19:1 and dried at 50° C./15 mbar for about 17 hours. 7.02 g of crystals of afatinib dimaleate were obtained. The obtained product was analyzed by PXRD.

Example 5

Preparation of AFT Dimaleate Form M

A small glass vessel with 76 mg of afatinib dimaleate form G (prepared according to the procedure described in example 4) in a fine layer was immersed in an oily bath and heated at 135-140° C. After 30 minutes, sample was cooled to 20° C.-25° C. Crystals of afatinib dimaleate were obtained. The obtained product was analyzed by PXRD.

Example 6

Preparation of AFT Dimaleate Form M

A small glass vessel with 305 mg of afatinib dimaleate form G (prepared according to the procedure described in example 4) in a fine layer was immersed in an oily bath and heated at 135-140° C. After 50 minutes, sample was cooled to 20-25° C. Crystals of afatinib dimaleate were obtained. The obtained product was analyzed by PXRD (FIG. 3).

Example 7

Preparation of AFT Dimaleate Form M

About 35 mg of afatinib dimaleate form G (prepared according to the procedure described in example 2) was suspended in 2.0 ml of THF and stirred at 150 rpm at 20° C.-25° C. for about 20 hours. Crystals were filtered off and dried at 50° C./15 mbar for about 17 hours. Crystals of afatinib dimaleate were obtained. The obtained product was analyzed by PXRD.

Example 8

Preparation of AFT Dimaleate Form M 0.150 g of afatinib dimaleate form G (prepared according to the procedure described in example 4) was suspended in 3.0 ml of nonane and heated at about 135° C. for about 1 hour. Crystals were filtered off and dried at room temperature for about 1 hour. Crystals of afatinib dimaleate were obtained. The obtained product was analyzed by PXRD.

Example 9

Preparation of AFT Dimaleate Form N

To a solution of 0.10 g of afatinib base (prepared according to the procedure described in example 1B) in 0.25 ml of tetrahydrofurane at 20° C.-25° C., a solution of 0.049 g of 99% maleic acid in 0.25 ml of tetrahydrofurane at 20° C.-25° C. was added. Obtained suspension was stirred for about 21.5 h hours at 20° C.-25° C., small amount of the suspension was filtrated off, crystals were dried at 50° C./15 mbar for about 3 hours, where crystals of afatinib dimaleate were obtained and to a rest of suspension, 2.0 ml of tetrahydrofurane was added and stirred for next 3.8 hours. Crystals were filtered off, washed with 1.0 ml of tetrahydrofurane and dried at 50° C./15 mbar for about 19 hours. 0.077 g of afatinib dimaleate were obtained. The obtained product was analyzed by PXRD.

Example 10

Preparation of AFT Dimaleate Form N

To a solution of 0.10 g of afatinib base (prepared according to the procedure described in example 1A) in 0.25 ml of tetrahydrofurane at 20° C.-25° C., seeded with small amount of afatinib dimaleat form N crystals (prepared according to the procedure described in example 9) a solution of 0.049 g of 99% maleic acid in 0.25 ml of tetrahydrofurane at 20° C.-25° C. was added. To an obtained suspension, 2.00 ml of tetrahydrofurane was added and seeded again with small amount of afatinib dimaleat form N crystals (prepared according to the procedure described in example 9). Obtained reaction mixture was stirred for about 21 hours at 20° C.-25° C., filtered off, crystals were washed with 1.0 ml of tetrahydrofurane and dried at 50° C./15 mbar/for about 4 hours. 0.091 g of crystals of afatinib dimaleate were obtained. The obtained product was analyzed by PXRD (FIG. 5).

Example 11

Preparation of AFT Dimaleate Form N

To a solution of 0.10 g of afatinib base (prepared according to the procedure described in example 1B) in 0.25 ml of tetrahydrofurane at 20° C.-25° C., seeded with small amount of afatinib dimaleat form N crystals (prepared according to the procedure described in example 9) a solution of 0.049 g of 99% maleic acid in 0.25 ml of tetrahydrofurane at 20° C.-25° C. was added. To the obtained suspension, 2.0 ml of tetrahydrofurane was added. The reaction mixture was stirred for about 21 hours at 20° C.-25° C., filtered off, crystals were washed with 1.0 ml of tetrahydrofurane and dried at 50° C./15 mbar for about 4 hours. 0.10 g of crystals of afatinib dimaleate were obtained. The obtained product was analyzed by PXRD.

Example 12

Preparation of AFT Dimaleate Form N

To a solution of 0.50 g of afatinib base (prepared according to the procedure described in example 1A) in 1.27 ml of tetrahydrofurane at 20° C.-25° C., seeded with small amount of afatinib dimaleat form N crystals (prepared according to the procedure described in example 11) a solution of 0.245 g of 99% maleic acid in 1.27 ml of tetrahydrofurane at 20° C.-25° C. was added. To the obtained suspension, 10.0 ml of tetrahydrofurane was added and seeded again with small amount of afatinib dimaleat form N crystals (prepared according to the procedure described in example 11). Obtained reaction mixture was stirred for about 4.5 hours at 20° C.-25° C., filtered off, crystals were washed two times with 1.0 ml of tetrahydrofurane and dried at 50° C./15 mbar 17 hours. 0.65 g of crystals of afatinib dimaleate were obtained. The obtained product was analyzed by PXRD.

Example 13

Preparation of AFT Dimaleate Form Alpha

To a solution of 8.15 g of afatinib base (prepared according to the procedure described in example 1A) in 115.0 ml of abs. ethanol at about 70° C., 1.0 g of charcoal was added, stirred for about 15 minutes and hot filtrated. To the filtrate, solution of 4.0 g of 99% maleic acid in 50.0 ml of abs. ethanol at about 70° C. was added. Obtained suspension was stirred for about 30 minutes at about 70° C., cooled down to a room temperature (20° C.-25° C.), stirred for about 20 hours and finally cooled to 0° C.-5° C. and stirred for about 4 hours. Crystals were filtered off, washed with 25.0 ml of absolute ethanol and dried at 40° C./vacuum for about 17 hours. 8.63 g of crystals of afatinib dimaleate were obtained. The obtained product was analyzed by PXRD.

Example 14

Preparation of AFT Dimaleate Form Alpha

To a solution of 8.15 g of afatinib base (prepared according to the procedure described in example 1A) in 115.0 ml of 96% ethanol at about 70° C., 1.0 g of charcoal was added, stirred for about 15 minutes and hot filtrated. To the filtrate, solution of 4.0 g of 99% maleic acid in 50.0 ml of 96% ethanol at about 70° C. was added. Obtained solution was stirred for about 45 minutes at about 70° C., cooled down to a room temperature (20° C.-25° C.), stirred for about 20 hours and finally cooled to 0° C.-5° C. and stirred for about 4 hours. Obtained crystals were filtered off, washed with 25.0 ml of 96% ethanol and dried at 40° C./vacuum for about 17 hours. 8.16 g of crystals of afatinib dimaleate were obtained. The obtained product was analyzed by PXRD.

Example 15

Preparation of AFT Dimaleate Form Alpha

To a solution of 0.50 g of afatinib base (prepared according to the procedure described in example 1A) in 3.0 ml of methanol at 45° C.-50° C., solution of 0.245 g of 99% maleic acid in 3.0 ml of methanol at about 45° C.-50° C. was added. Obtained solution was stirred for 1 hour at 45° C.-50° C., cooled down to a room temperature (20° C.-25° C.), stirred for about 1 hour and finally cooled to 0° C.-5° C. and stirred for about 1 hour. Obtained crystals were filtered off, washed with 2×2.0 ml of cold methanol and dried at 50° C./15 mbar for about 17 hours. 0.57 g of crystals of afatinib dimaleate were obtained. The obtained product was analyzed by PXRD (FIG. 7).

Example 16

Preparation of AFT Dimaleate Form Alpha

To a solution of 0.50 g of afatinib base (prepared according to the procedure described in example 1A) in 12.0 ml of ethyl acetate/methanol, 9:1 at about 60° C., solution of 0.245 g of 99% maleic acid in 3.0 ml of ethyl acetate/methanol, 9:1 at about 60° C. was added. Obtained suspension was stirred for 1 hour at about 60° C., cooled down to a room temperature (20° C.-25° C.), stirred for about 1 hour and finally cooled to 0° C.-5° C. and stirred for about 2 hours. Obtained crystals were filtered off, washed with 2.0 ml of ethyl acetate/methanol, 9:1 and dried at 40° C./15 mbar for about 17 hours. 0.65 g. The obtained product was analyzed by PXRD.

Example 17

Preparation of AFT Dimaleate Form Alpha 0.5 g of AFT base form C (prepared according to the procedure described in example 1C-C was dissolved in 7 ml of EtOH, abs. After 5 minutes of stirring, crystallization occurred. In suspension at 20-25° C., solution of 0.23 g of maleic acid in 3 ml of ethanol, abs. was added. At the end of maleic acid addition, some oiling was noticed in reaction mixture. Suspension was stirred 0.5 h at 20° C. and 1.5 h at 0-5° C. Crystals were filtered, washed with ethanol, abs. and dried at 50° C. under reduced pressure to obtain 0.57 g of AFT dimaleate form Alpha. The obtained product was analyzed by PXRD.

Example 18

Preparation of AFT Dimaleate Form Alpha 0.5 g of AFT base form C (prepared according to the procedure described in example 1C-C) was dissolved in 7 ml of EtOH, 96% by heating at 70° C. Solution of 0.23 g of maleic acid was added at the same temperature. Solution was cooled down at 0-5° C. when crystallization occurred. Suspension was stirred for 1.5 hours and filtered. Crystals were dried at 50° C. under reduced pressure to obtain 0.58 g of AFT dimaleate form Alpha. The obtained product was analyzed by PXRD.

Example 19

Preparation of AFT Dimaleate Form Alpha 22.0 g of Afatinib base form C (prepared according to the procedure described in example 1C-C) was dissolved in 100 ml of methanol at 47° C. Solution of 10.9 g maleic acid in 100 ml methanol was added at the same temperature. Clear solution was cooled at 40° C. and seeded with crystals of form alpha (prepared according to the procedure described in example 18). Crystallization occurred immediately. Suspension was cooled at 20-25° C., stirred for 2 hours, cooled at 0-5° C. and stirred for additional 1 hour. Crystals were filtered, washed with methanol and dried at 50° C. under reduced pressure to obtain 27.5 g of AFT dimaleate form Alpha. The obtained product was analyzed by PXRD.

Example 20

Preparation of AFT Dimaleate Form M 4.0 g of Afatinib dimaleate form G was suspended in 80 ml of n-nonane. Suspension was heated at 120° C., stirred for about 20-25 minutes and cooled at 20° C. Crystals were filtered, washed with n-nonane and dried at 50° C. under reduced pressure to obtain 3.7 g of AFT dimaleate form M. The obtained product was analyzed by PXRD.

Example 21

Preparation of AFT Dimaleate Form M 0.50 g of AFT base form C (prepared according to the procedure described in example 1C-C) was dissolved in 10 ml of THF. Solution was cooled at 0-5° C. and seeded with crystals of form M (prepared according to the procedure described in example 20). Solution of 0.224 g of maleic acid in 2.5 ml THF was added slowly. Crystallization occurred during addition of acid. Suspension was stirred at 0-5° C. for 3.5 hours, heated at 20-25° C. and stirred for additional 18 h. Crystals were filtered, washed with THF and dried at 50° C. under reduced pressure for 4 hours to obtain 0.61 g of Afatinib dimaleate form M. The obtained product was analyzed by PXRD.

Example 22

Preparation of AFT Dimaleate Form M 1.00 g of Afatinib dimaleate form G was suspended in 20 ml of n-nonane. Suspension was heated at 110° C., stirred for 25 minutes, cooled down at 0-5° C. and stirred for additional 2 hours. Crystals were filtered, washed with n-nonane and dried at 50° C. under reduced pressure to obtain 0.95 g of AFT dimaleate form M. The obtained product was analyzed by PXRD.

Example 23

Preparation of AFT Dimaleate Form N 0.50 g of Afatinib base form C (prepared according to the procedure described in example 1C-C) was dissolved in 10 ml of THF. Solution was cooled at 0-5° C. and seeded with crystals of form N (prepared according to the procedure described in example 9). Solution of 0.226 g of maleic acid in 2.5 ml THF was added slowly. Obtained suspension was stirred at 0-5° C. for 3.5 hours, heated at 20° C. and stirred for additional 20 hours. Crystals were filtered, washed with THF and dried at 50° C. under reduced pressure to obtain 0.65 g of AFT dimaleate form N. The obtained product was analyzed by PXRD.

What is claimed is:
1. A crystalline form of Afatinib di-maleate, wherein the crystalline form is:

a crystalline form of Afatinib di-maleate designated as form Alpha, characterized by data selected from one or more of the following:

X-ray powder diffraction pattern having peaks at 6.6, 10.6, 15.3, 16.3 and 24.2 degrees two theta±0.2 degrees two theta;

an X-ray powder diffraction pattern as depicted in FIG. 7;

a solid state $^{13}$C NMR spectrum with signals at about 171.6, 129.6, 102.4 and 79.0±0.2 ppm;

a solid state $^{13}$C NMR spectrum as depicted in FIG. 17; and combinations of these data.

2. The crystalline Form Alpha according to claim 1, characterized by a PXRD pattern having peaks at 6.6, 10.6, 15.3, 16.3 and 24.2 degrees 2-theta±0.2 degrees 2-theta.

3. The crystalline Form Alpha according to claim 2, further characterized by a PXRD pattern having one, two, three, four or five additional peaks selected from: 13.3, 13.8, 17.0, 17.3 and 27.1 degrees two theta±0.2 degrees two-theta;

a DSC thermogram as depicted in FIG. 8;

a Raman spectrum having characteristic peaks at 3041, 1686, 1390, 1234 and 602±4 cm−1;

a Raman spectrum substantially as depicted in FIG. 18; and combinations of these data.

4. The crystalline Form Alpha according to claim 1, wherein said form is anhydrous.

* * * * *